(12) United States Patent
Chiari et al.

(10) Patent No.: US 11,230,732 B2
(45) Date of Patent: Jan. 25, 2022

(54) GENOTYPING OF MUTATIONS BY COMBINATION OF IN-TUBE HYBRIDIZATION AND UNIVERSAL TAG-MICROARRAY

(71) Applicants: Marcella Chiari, Milan (IT); Francesco Damin, Busto Arsizio (IT); Silvia Galbiati, Cernusco sul Naviglio (IT); Maurizio Ferrari, Milan (IT)

(72) Inventors: Marcella Chiari, Milan (IT); Francesco Damin, Busto Arsizio (IT); Silvia Galbiati, Cernusco sul Naviglio (IT); Maurizio Ferrari, Milan (IT)

( * ) Notice: Subject to any disclaimer, the term of this patent is extended or adjusted under 35 U.S.C. 154(b) by 0 days.

(21) Appl. No.: 16/493,607

(22) PCT Filed: Mar. 30, 2018

(86) PCT No.: PCT/IB2018/052219
§ 371 (c)(1),
(2) Date: Sep. 12, 2019

(87) PCT Pub. No.: WO2018/178943
PCT Pub. Date: Oct. 4, 2018

(65) Prior Publication Data
US 2020/0102605 A1    Apr. 2, 2020

Related U.S. Application Data
(60) Provisional application No. 62/479,995, filed on Mar. 31, 2017.

(51) Int. Cl.
*C12Q 1/6837* (2018.01)
*C12Q 1/6827* (2018.01)

(52) U.S. Cl.
CPC ......... *C12Q 1/6837* (2013.01); *C12Q 1/6827* (2013.01); *C12Q 2535/131* (2013.01); *C12Q 2537/125* (2013.01); *C12Q 2565/514* (2013.01)

(58) Field of Classification Search
CPC ............................ C12Q 1/6837; C12Q 1/6827
See application file for complete search history.

(56) References Cited

U.S. PATENT DOCUMENTS

2004/0059519 A1* 3/2004 Chandler ................. C12Q 1/00
702/19
2010/0041563 A1* 2/2010 Li ........................ C12Q 1/6883
506/9

FOREIGN PATENT DOCUMENTS

WO    WO 00/50869 A2    8/2000
WO    WO 00/61817 A1    10/2000
WO    WO 2011/080068 A1    7/2011

OTHER PUBLICATIONS

Negru et al, KRAS, NRAS and BRAF mutations in Greek and Romanian patients with colorectal cancer: a cohort study, 2014, BMJ Open, 4:e004652, pp. 1-8 (Year: 2014).*
Semi et al , High-Resolution Melting Analysis for Rapid Detection of KRAS, BRAF, and PIK3CA Gene Mutations in Colorectal Cancer, 2008, Am J Clin Pathol, 130, 247-253. (Year: 2008).*
Wang et al, An automated microfluidic system for single-stranded DNA preparation and magnetic bead-based microarray analysis, 2015, Biomicrofluidics , 9, 024102, pp. 1-17 (Year: 2015).*
Batistella, Stefania, et al. "Genotyping β-Globin Gene Mutations on Copolymer-Coated Glass Slides with the Ligation Detection Reaction." Clinical Chemistry, vol. 54, No. 10, pp. 1657-1663 (Aug. 14, 2008).
Galbiati, Silvia, et al. "A New Microarray Substrate for Ultra-Sensitive Genotyping of KRAS and BRAF Gene Variants in Colorectal Cancer." PLoS ONE, vol. 8, No. 3, p. e59939 (Mar. 25, 2013). doi:10.1371/journal.pone.0059939.
Gerry, Norman P., et al. "Universal DNA Microarray Method for Multiplex Detection of Low Abundance Point Mutations." J. Mol. Biol., vol. 292, No. 2, pp. 251-262 (Dec. 31, 1999).
Allegra, C. J. et al. American Society of Clinical Oncology provisional clinical opinion: testing for KRAS gene mutations in patients with metastatic colorectal carcinoma to predict response to anti-epidermal growth factor receptor monoclonal antibody therapy. J. Clin. Oncol. 27, 2091-6 (2009).
Cretich, M. et al. High sensitivity protein assays on microarray silicon slides. Anal. Chem. 81, 5197-203 (2009).
Damin, F., Galbiati, S., Ferrari, M. & Chiari, M. DNA microarray-based solid-phase PCR on copoly (DMA-NAS-MAPS) silicon coated slides: An example of relevant clinical application. Biosens. Bioelectron. 78, 367-373 (2016).

(Continued)

*Primary Examiner* — Narayan K Bhat
(74) *Attorney, Agent, or Firm* — The Marbury Law Group, PLLC

(57) ABSTRACT

An assay for detecting gene fragments, including: amplifying gene fragments comprising single-nucleotide polymorphisms (SNPs) to form an initial amplification product; isolating single strand oligonucleotides of interest from the initial amplification product; forming a solution comprising the oligonucleotides of interest and reporter molecules, each reporter molecule having a first oligonucleotide domain configured to hybridize with a complementary oligonucleotide of interest, and a second oligonucleotide domain configured to hybridize with a complementary capture probe; hybridizing, in the solution, the oligonucleotides of interest with the reporter molecules that have complementary first domains; applying the solution to the surface of a microarray including an array of capture probes fixed to a microarray slide; capturing the oligonucleotides of interest on the microarray by hybridizing the second oligonucleotide domains of the reporter molecules with complementary capture probes of the microarray; and detecting the hybridized oligonucleotides of interest captured on the microarray.

21 Claims, 15 Drawing Sheets
Specification includes a Sequence Listing.

(56) References Cited

OTHER PUBLICATIONS

Dieterle, C. P., Conzelmann, M., Linnemann, U. & Berger, M. R. Detection of Isolated Tumor Cells by Polymerase Chain Reaction-Restriction Fragment Length Polymorphism for K-ras Mutations in Tissue Samples of 199 Colorectal Cancer Patients. Clin. Cancer Res. 10, (2004).
Favis, R., Gerry, N. P., Cheng, Y.-W. & Barany, F. Applications of the universal DNA microarray in molecular medicine. Methods Mol. Med. 114, 25-58 (2005).
Gentalen, E. & Chee, M. A novel method for determining linkage between DNA sequences: hybridization to paired probe arrays. Nucleic Acids Res. 27, 1485-91 (1999).
Herreros-Villanueva, M., et al. KRAS mutations: analytical considerations. Clin. Chim. Acta. 431, 211-20 (2014).
Hoffman, M. Getting a handle on Ras activity. Science, vol. 255, Issue 5041, p. 159 (Jan. 10, 1992).
Huang, J. X. et al. High-Throughput Genomic and Proteomic Analysis Using Microarray Technology. Clin. Chem. 47, (2001).
Huggett, J. F. & Whale, A. Digital PCR as a novel technology and its potential implications for molecular diagnostics. Clin. Chem. 59, 1691-3 (2013).
Jacobson, D. R. & Mills, N. E. A highly sensitive assay for mutant ras genes and its application to the study of presentation and relapse genotypes in acute leukemia. Oncogene 9, 553-63 (1994). (abstract only).
Karapetis CS, Maru D, Waring P, Tie J, Michael MZ. Incorporating traditional and emerging biomarkers in the clinical management of metastatic colorectal cancer, Expert Review of Molecular Diagnostics, 2015;15:1033-48.
Kiaris, H. & Spandidos, D. Mutations of Ras Genes in Human Tumors (Review). Int. J. Oncol. (1995). doi:10.3892/ijo.7.3.413.
LaFramboise, T. Single nucleotide polymorphism arrays: a decade of biological, computational and technological advances. Nucleic Acids Res. 37, 4181-4193 (2009).
Lin, M.-T. et al. Clinical Validation of KRAS, BRAF, and EGFR Mutation Detection Using Next-Generation Sequencing. Am. J. Clin. Pathol. 141, (2014).
Liu, Y., Gudnason, H., Li, Y., Bang, D. D. & Wolff, A. An oligonucleotide-tagged microarray for routine diagnostics of colon cancer by genotyping KRAS mutations. 1556-1564 (2014). doi:10.3892/ijo.2014.2541.
Lopez-Crapez, E., Chypre, C., Saavedra, J., Marchand, J. & Grenier, J. Rapid and large-scale method to detect K-ras gene mutations in tumor samples. Clin. Chem. 43, 936-42 (1997).
Luo, J.-D. et al. Detection of rare mutant K-ras DNA in a single-tube reaction using peptide nucleic acid as both PCR clamp and sensor probe. Nucleic Acids Res. 34, e12 (2006).
Maekawa, M. et al. Three-Dimensional Microarray Compared with PCR-Single-Strand Conformation Polymorphism Analysis/DNA Sequencing for Mutation Analysis of K-ras Codons 12 and 13. Clin. Chem. 50, (2004).
Mixich, F., Ioana, M., Voinea, F., Săftoiu, A. & Ciurea, T. Noninvasive detection through REMS-PCR technique of K-ras mutations in stool DNA of patients with colorectal cancer. J. Gastrointestin. Liver Dis. 16, 5-10 (2007).
Pajic, M., et al. Preclinical strategies to define predictive biomarkers for therapeutically relevant cancer subtypes. Hum. Genet. 130, 93-101 (2011).
Parsons, B. L. et al. ACB-PCR Quantification of K-RAS Codon 12 GAT and GTT Mutant Fraction in Colon Tumor and Non-Tumor Tissue. Cancer Invest. 28, 364-375 (2010).
Pirri, G., Damin, F., Chiari, M., Bontempi, E. & Depero, L. E. Characterization of a polymeric adsorbed coating for DNA microarray glass slides. Anal. Chem. 76, 1352-8 (2004).
Sham, P. C. et al. Whole-genome association studies of complex diseases. Curr. Orthop. 22, 251-258 (2008).
Shirasawa, S., et al., Altered growth of human colon cancer cell lines disrupted at activated Ki-ras. Science (80-. ). 260, (1993).
Toyooka, S. et al. Detection of codon 61 point mutations of the K-ras gene in lung and colorectal cancers by enriched PCR. Oncol. Rep. 10, 1455-9 (2003).
Tsiatis, A. C. et al. Comparison of Sanger Sequencing, Pyrosequencing, and Melting Curve Analysis for the Detection of KRAS Mutations: Diagnostic and Clinical Implications. (2010). doi:10.2353/jmoldx.2010.090188.
Wang, J. et al. Direct sequencing is a reliable assay with good clinical applicability for KRAS mutation testing in colorectal cancer. Cancer Biomark. 13, 89-97 (2013).
Yanez, L., Groffen, J. & Valenzuela, D. M. c-K-ras mutations in human carcinomas occur preferentially in codon 12. Oncogene 1, 315-8 (1987).

* cited by examiner

Operation times

GENOTYPING OF MUTATIONS BY COMBINATION OF IN-TUBE HYBRIDIZATION AND UNIVERSAL TAG-MICROARRAY

INCORPORATION BY REFERENCE OF SEQUENCE LISTING

This application incorporates by reference the sequence listing in the ASCII text file entitled "3015 004WO SL", created on Jun. 8, 2018, file size 23 KB. This sequence listing has been filed at the U.S. Patent and Trademark Office with the other documents for this application.

BACKGROUND

The identification of DNA variants that can cause diseases is a central aim in human genetics. In particular, the ability to detect mutations linked to malignant diseases facilitates early diagnosis, prevention and treatment[1,2]. The low-frequency single nucleotide mutations detection in a cancer biopsy sample is challenging, as it requires the discrimination between two highly similar sequences, one of which (the wild-type sequence) is significantly more abundant than the other[3].

Liquid biopsy is a term coined to describe an emerging class of blood tests meant to replace tissue biopsy for obtaining diagnostic, prognostic, and theranostic information concerning cancer. Liquid biopsies could allow physicians to gain a systemic view of patient-specific cancers as well as the ability to monitor them over time. Using blood, urine, saliva, cerebrospinal fluid, pleural effusions rather than tissue, it is possible to detect cancer causing genomic alterations by analyzing circulating tumor DNA (ctDNA). The detection of low-frequency single nucleotide mutations in a liquid biopsy sample is even more challenging than in a tissue biopsy as ctDNA accounts for less than 1% of total circulating free DNA in the blood. Therefore standard sequencing techniques, such as Sanger sequencing or pyrosequencing, can detect ctDNA only among patients with heavy tumor burden. The introduction of digital polymerase chain reaction has enabled the detection of ctDNA in a considerably consistent manner.

In particular, the droplet digital PCR (ddPCR) is one of newly developed methods that allow for enumeration of rare mutant variants in complex mixtures of DNA (wild-type and mutant DNA). Based on water-emulsion droplet technology, ddPCR fractionates a DNA sample in, for example, 20,000 droplets. Mutation-specific amplification of the template subsequently occurs in each individual droplet, and counting the positive droplets gives precise, absolute target quantification as copies per milliliter of plasma. It was been reported that ddPCR can detect mutant alleles with high sensitivity (0.01-0.001%). However, the method lacks of multiplexing capability.

Another sophisticated and costly ctDNA based cancer test is the targeted amplicon sequencing. Recently this technology has been proposed to favor the translation from basic research to clinical practice. Indeed, Next Generation Sequencing (NGS) in particular conditions can reach the high sensitivity required for the analysis of ctDNA, but it is expensive and time-consuming. Moreover, it allows to process in parallel only a limited number of samples and demands bioinformatics skills or already developed bioinformatics tools specific for plasma samples.

In recent years, many additional efforts have been made to develop other highly specific and sensitive techniques for the detection of low-abundance mutations, including real-time PCR, coamplification at lower denaturation temperature-PCR (COLD-PCR), pyrosequencing, digital PCR[3,4] and NGS. Each of these methodologies has advantages and disadvantages. In this scenario, the microarray based approach proposed in this work represents a versatile tool for high-throughput detection of single nucleotide mutations[5-7].

In digestive organs and lung cancers, various activating point mutations of the KRAS oncogene are frequently detected. In tumorigenesis they are thought to alter the GTPase activity, leading to unregulated cellular proliferation and malignant transformation[8-10]. The most common mutations are clustered in a very narrow region located at codons 12 and 13[11] in exon 2. These sites are considered mutational hot spots in carcinogenesis. Although mutated KRAS is currently the only biomarker with a US FDA-approved companion diagnostic test for metastatic colorectal cancer (mCRC)[12], a number of emerging biomarkers (NRAS, BRAF and PIK3CA) may prove to be clinically useful.

Various methods have been used to identify KRAS gene mutations, such as direct DNA sequencing[13], next-generation sequencing[14], mutant enriched polymerase chain reaction (PCR)[15], peptide nucleic acid (PNA)-based PCR[16], restriction endonuclease-mediated selective (REMS)-PCR[17], PCR-restriction fragment length polymorphism (PCR-RFLP)[18], mutation tube assay (MUTA) test[19], allele-specific competitive blocker PCR (ABC-PCR)[20]. However, these approaches are time-consuming and cost-ineffective requiring laborious procedural manipulations.

DNA microarrays have been used for years in genotyping applications, including SNP typing (SNP is "single-nucleotide polymorphism"). For instance, Affymetrix and Illumina commercialize SNP array platforms for the genotyping of millions of SNPs[7], but, they are mostly applied in the research activity. To the best of our knowledge, there are only few examples of KRAS genotyping by microarray technique. They include the PamChip microarray[21], the oligonucleotide-tagged microarray reported by Liu et al.[22] and the "zip-code array" in combination with polymerase chain reaction/ligase detection reaction (PCR/LDR)[23,24]. The sensitivity of these assays in the detection of KRAS codon 12 mutations is low, ranging from 25-10% to a minimum of 1% in the case of PCR/LDR. To improve sensitivity, in a previous work[25], an assay was developed based on the "amplicon down" approach on a layered silicon/silicon oxide substrate for microarray coated with a copolymer of dimethylacrylamide (DMA), N-acryloyloxysuccinimide (NAS) and meta-acryloy propyl trimethoxy silane (MAPS), copoly(DMA-NAS-MAPS).[26,27] The polymer forms a tri-dimensional functional coating on the surface of the slide able to bind amino-modified oligonucleotide with high density. This assay format proved to be highly specific in assigning the correct genotyping of the KRAS mutations. In spite of the positive results, that approach had a major drawback as it required spotting PCR products by a commercial arrayer not available to most clinical laboratories. To overcome this issue, a solid-phase PCR assay was introduced in which the amplicons were produced in-situ on the slide surface[28]. The method circumvented the need of depositing of PCR fragment but lacked the desired sensitivity being able to detect mutated allele only at 1% in the wild-type DNA background.

Clearly, a need exists for better, more accurate, more sensitive, and/or more rapid assay methods and/or compositions to accomplish these and other goals.

SUMMARY

Various aspects and embodiments for methods, compositions, systems, and/or kits are described and/or claimed herein. The methods include methods of making and methods of use.

In an attempt to overcome the limitations of past approaches such as, for example, ddPCR and targeted amplicon sequencing, a new method based on, in preferred embodiments, in-tube specific hybridization between single stranded tagged-PCR products and specific dual-domain oligonucleotide reporters combined with surface capture at specific microarray locations (2D-array) is disclosed.

For example, a first aspect is for an assay method for a gene fragment of interest comprising:

amplify at least one gene fragment of interest comprising or potentially comprising at least one SNP region of interest to form an initial amplification product;

forming at least one single strand amplification product from the initial amplification product, wherein the single strand amplification product either comprises or potentially comprises the at least one SNP region of interest;

hybridize in solution the single strand amplification product with at least one reporter molecule which comprises at least two, different domains of oligonucleotide, wherein a first domain of oligonucleotide is for hybridization with the single strand amplification product, and wherein the second domain of oligonucleotide is for hybridization to at least one microarray probe surface, wherein the microarray probe surface comprises at least one capture probe to allow for hybridization;

contact the solution of the hybridized single strand amplification product with the at least one microarray probe surface which comprises at least one capture probe to allow for hybridization;

detect for the presence of the hybridized single strand amplification product on the microarray surface. In one embodiment, the fragment to be amplified is primed in the amplification to enable detection of the isolated single strand in a later step in the assay. In another embodiment, the fragment to be amplified is primed in the amplification to enable (1) isolation of one single strand from another single strand of the initial amplification product in a later step of the assay, and (2) detection of the isolated single strand in a later step in the assay. In another embodiment, forming the at least one single strand amplification product from the initial amplification product, wherein the single strand amplification product either comprises or potentially comprises the at least one SNP region of interest, comprises isolating the single strand amplification product.

In another example, a second aspect provides for an assay method for a gene fragment of interest comprising:

amplify at least one gene fragment of interest comprising or potentially comprising at least one SNP region of interest to form an initial amplification product, wherein the fragment to be amplified is primed in the amplification to enable (1) isolation of one single strand from another single strand of the initial amplification product in a later step of the assay, and (2) detection of the isolated single strand in a later step in the assay;

isolate at least one single strand amplification product from the initial amplification product, wherein the single strand amplification product either comprises or potentially comprises the at least one SNP region of interest;

hybridize in solution the single strand amplification product with at least one reporter molecule which comprises at least two, different domains of oligonucleotide, wherein a first domain of oligonucleotide is for hybridization with the single strand amplification product, and wherein the second domain of oligonucleotide is for hybridization to at least one microarray probe surface, wherein the microarray probe surface comprises at least one capture probe to allow for hybridization;

contact the solution of the hybridized single strand amplification product with the at least one microarray probe surface which comprises at least one capture probe to allow for hybridization;

detect for the presence of the hybridized single strand amplification product on the microarray surface. In some embodiments, the assay and the gene fragment of interest are for the detection of at least one single mutation in a KRAS, NRAS, BRAF, and/or PIK3CA oncogene.

Another example is a third aspect for an assay method for a KRAS, NRAS, BRAF, and/or PIK3CA oncogene fragment of interest comprising:

amplify at least one KRAS, NRAS, BRAF, and/or PIK3CA oncogene fragment of interest comprising or potentially comprising at least one SNP region of interest to form an initial amplification product;

form at least one single strand amplification product from the initial amplification product with use of denaturation and coupling to a bead, wherein the single strand amplification product either comprises or potentially comprises the at least one SNP region of interest, wherein optionally the isolated single strand amplification product is stabilized before further hybridization;

hybridize in solution the single strand amplification product with at least one reporter molecule which comprises at least two, different domains of oligonucleotide, wherein a first domain of oligonucleotide is for hybridization with the single strand amplification product, and wherein the second domain of oligonucleotide is for hybridization to at least one microarray probe surface, and wherein the hybridization step comprises application of a temperature gradient covering at least two different hybridization temperatures, and wherein the microarray probe surface comprises at least one capture probe to allow for hybridization;

contact the solution of the hybridized single strand amplification product with the at least one microarray probe surface which comprises at least one capture probe to allow for hybridization;

detect with fluorescence for the presence of the hybridized single strand amplification product on the microarray surface.

More particularly, a fourth aspect is for an assay method for a KRAS, NRAS, BRAF, and/or PIK3CA oncogene fragment of interest comprising:

amplify at least one KRAS, NRAS, BRAF, and/or PIK3CA oncogene fragment of interest comprising or potentially comprising at least one SNP region of interest to form an initial amplification product, wherein the fragment to be amplified is primed in the amplification to enable (1) isolation of one single strand from another single strand of the initial amplification product by coupling to a bead in a later step of the assay, and (2) detection of the isolated single strand by fluorescent detection in a later step in the assay;

isolate at least one single strand amplification product from the initial amplification product with use of denaturation and coupling to a bead, wherein the single strand amplification product either comprises or potentially comprises the at least one SNP region of interest, wherein optionally the isolated single strand amplification product is stabilized before further hybridization;

hybridize in solution the single strand amplification product with at least one reporter molecule which comprises at least two, different domains of oligonucleotide, wherein a first domain of oligonucleotide is for hybridization with the single strand amplification product, and wherein the second domain of oligonucleotide is for hybridization to at least one microarray probe surface, and wherein the hybridization step comprises application of a temperature gradient covering at least two different hybridization temperatures, and wherein the microarray probe surface comprises at least one capture probe to allow for hybridization;

contact the solution of the hybridized single strand amplification product with the at least one microarray probe surface which comprises at least one capture probe to allow for hybridization;

detect with fluorescence for the presence of the hybridized single strand amplification product on the microarray surface. In one embodiment, the optional step is carried out such that the isolated single strand amplification product is stabilized before further hybridization.

In some embodiments, the assay and the gene fragment of interest are for the detection of at least one single mutation in a KRAS oncogene. In some embodiments, the assay and the gene fragment of interest are for the detection of at least one KRAS oncogene mutation at codon 12, and/or codon 13, and/or codon 61, and/or codon 146. In some embodiments, the assay and the gene fragment of interest are for the detection of at least one KRAS oncogene mutation at codon 12 and/or codon 13. In some embodiments, the assay and the gene fragment of interest are for detection of at least one KRAS oncogene mutation which includes at least one of G12A, G12C, G12D, G12R, G12S, and/or G12V in codon 12; and/or G13D in codon 13; and/or Q61HC Q61HT, Q61 L, Q61R, and/or Q61K in codon 61; and/or A146T in codon 146 mutations.

In other embodiments, the assay and the gene fragment of interest are for detection of at least one single mutation in an NRAS oncogene. In some embodiments, the assay and the gene fragment of interest are for detection of at least one NRAS oncogene mutation at codon 12 and/or codon 13. In some embodiments, the assay and the gene fragment of interest are for detection of at least one NRAS oncogene mutation which includes at least one of G12A, G12C, G12D, G12S, G12V in codon 12, and/or G13D, G13R, G13V in codon 13 mutations.

In other embodiments, the assay and the gene fragment of interest are for the detection of at least one single mutation in a BRAF oncogene. In some embodiments, the assay and the gene fragment of interest are for the detection of at least one BRAF mutation at codon 600. In some embodiments, the assay and the gene fragment of interest are for the detection of one BRAF oncogene mutation which is the V600 E in codon 600 mutation.

In other embodiments, the assay and the gene fragment of interest are for the detection of at least one single mutation in a PIK3CA oncogene. In some embodiments, the assay and the gene fragment of interest are for the detection of at least one PIK3CA mutation at codon 542, 545, and/or 1047. In some embodiments, the assay and the gene fragment of interest are for the detection of at least one PIK3CA mutation which includes at least one of E542K in codon 542 mutation, E545K in codon 545 mutation, and/or H1047R in codon 1047 mutation.

In some embodiments, the initial amplification product is linked to a magnetic bead to enable the isolation of one single strand from another single strand of the initial amplification product in a later step of the assay. In another embodiment, the initial amplification product, linked to a bead, is subjected to separation by centrifugation or filtration. In such embodiments, the initial amplification product is made with use of a primer which bears, for example, biotin that allows to bind the amplification product to a bead coated with, for example, streptavidin to allow for further isolation and/or separation steps. Other specific binding examples besides biotin and stretavidin can be used as known in the art.

In other embodiments, the initial amplification product is linked to a tag which enables fluorescent detection of the isolated single strand in a later step in the assay. The tag can be, for example, an ologonucleotide sequence which will in a later step of the assay hybridize with, for example, a fluorescently labeled complementary sequence. In other embodiments, the initial amplification product is linked to particles which enable interferometric detection of the isolated single strand in a later step in the assay. For example, an oligonucleotide sequence can be used that will in a later step of the assay hybridize with a particle, such as a gold nanoparticle, which is labeled complementary sequence. This can enable, for example, interferometric detection of the isolated single strand in a later step in the assay. In some embodiments, the amplification step comprises PCR amplification.

In some embodiments, the isolation step comprises thermal denaturation of the initial amplification product and separation of the one single strand from the other single strand. In some embodiments, the isolation step comprises chemical denaturation of the initial amplification product and separation of the one single strand from the other single strand. In some embodiments, the hybridization step comprises application of a temperature gradient covering at least two different hybridization temperatures. In some embodiments, the hybridization step comprises hybridization of wild-type sequences. In some embodiments, isolated single strand amplification product is stabilized before further hybridization. In some embodiments, the conformation of the isolated single strand amplification product is stabilized by hybridization with an oligonucleotide whose sequence is adjacent to that encompassing the mutations before further hybridization.

In some embodiments, the microarray probe surface comprises at least seven, or at least eight, different capture probes. In some embodiments, the microarray probe surface comprises at least one terpolymer coating on the substrate surface which binds to the capture probe. In some embodiments, the microarray probe surface comprises at least one terpolymer coating on the substrate surface which binds to the capture probe, and which comprises at least one polymer backbone unit which is acrylamide or methacrylamide, at least one second polymer backbone unit which is adapted for binding to the substrate surface, and at least one third polymer backbone unit which binds to the capture probe. In some embodiments, the microarray probe surface comprises at least one terpolymer coating on the substrate surface which binds to the capture probe, and wherein the copolymer is further blocked to prevent non-specific binding during the assay.

In some embodiments, the detection step comprises at least one colorimetry, chemiluminescence, label free detection by surface plasmon resonance (SPR) or interferometry, or fluorescence detection step. In some embodiments, the detection step is a fluorescence detection step.

Other embodiments provide for a kit which is adapted for carrying out any of the assay method steps, or all of the assay method steps, described and/or claimed herein.

An additional aspect provides for a composition comprising at least one reporter molecule which comprises at least two, different domains of oligonucleotide, wherein a first domain of oligonucleotide is for hybridization with a single strand amplification product, and wherein the second domain of oligonucleotide is for hybridization to at least one microarray probe surface, and wherein the reporter molecule further comprises a core which is surface functionalized with the first domain and the second domain.

Still further, another aspect provides for an assay method for a gene fragment of interest comprising:

amplify at least one gene fragment of interest comprising or potentially comprising at least one SNP region of interest to form an initial amplification product, wherein the fragment to be amplified is primed in the amplification to enable (1) isolation of one single strand from another single strand of the initial amplification product in a later step of the assay, and (2) detection of the isolated single strand in a later step in the assay;

isolate at least one single strand amplification product from the initial amplification product, wherein the single strand amplification product either comprises or potentially comprises the at least one SNP region of interest;

hybridize in solution the single strand amplification product with at least one reporter molecule which comprises at least two, different domains of oligonucleotide, wherein a first domain of oligonucleotide is for hybridization with the single strand amplification product, and wherein the second domain of oligonucleotide is for hybridization to at least one microarray probe surface, wherein the microarray probe surface comprises at least one capture probe to allow for hybridization;

contact the solution of the hybridized single strand amplification product with the at least one microarray probe surface which comprises at least one capture probe to allow for hybridization;

detect for the presence of the hybridized single strand amplification product on the microarray surface, wherein the reporter molecule comprises a core which is surface functionalized with the first domain and the second domain.

Still further, another aspect provides for an assay method for a gene fragment of interest comprising:

amplify at least one gene fragment of interest comprising or potentially comprising at least one SNP region of interest to form an initial amplification product, wherein the fragment to be amplified is primed in the amplification to enable (1) isolation of one single strand from another single strand of the initial amplification product in a later step of the assay, and (2) detection of the isolated single strand in a later step in the assay;

isolate at least one single strand amplification product from the initial amplification product, wherein the single strand amplification product either comprises or potentially comprises the at least one SNP region of interest;

hybridize in solution the single strand amplification product with at least one reporter molecule which comprises at least two, different domains of oligonucleotide, wherein a first domain of oligonucleotide is for hybridization with the single strand amplification product, and wherein the second domain of oligonucleotide is for hybridization to at least one microarray probe surface, wherein the microarray probe surface comprises at least one capture probe to allow for hybridization;

contact the solution of the hybridized single strand amplification product with the at least one microarray probe surface which comprises at least one capture probe to allow for hybridization;

detect for the presence of the hybridized single strand amplification product on the microarray surface, wherein the reporter molecule is a composition comprising, consisting essentially of, or consisting of a composition as described and/or claimed herein for the reporter molecule.

In some embodiments, the core is a polymeric core. In some embodiments, the core is free on nucleotides. In some embodiments, the core is a water-soluble polymer core. In some embodiments, the core is a dendrimer core. In some embodiments, the core is a dendron core. In some embodiments, the core is covalently bound to the first domain and the second domain. In some embodiments, the core is an azido dendrimer core which is covalently bound to the first domain and the second domain. In some embodiments, the core is a dendrimer core which is covalently bound to the first domain and the second domain, and the ratio of the first domain to the second domain is about 10:1 to 1:1.

In some embodiments, the reporter molecule composition is adapted for use in a microarray assay for genotyping of a gene fragment of interest. In some embodiments, the composition is adapted for use in detection of a single mutation of an oncogene. In some embodiments, the composition is adapted for use in the detection of at least one single mutation in a KRAS, NRAS, BRAF, and/or PIK3CA oncogene. In some embodiments, the first domain is for the detection of at least one single mutation in a KRAS oncogene. In some embodiments, the first domain is for the detection of at least one KRAS oncogene mutation at codon 12, and/or codon 13, and/or codon 61, and/or codon 146. In some embodiments, the first domain is for the detection of at least one KRAS oncogene mutation at codon 12 and/or codon 13. In some embodiments, the first domain is for the detection of at least one KRAS oncogene mutation which includes at least one of G12A, G12O, G12D, G12R, G12S, and/or G12V in codon 12; and/or G13D in codon 13; and/or Q61HC Q61HT, Q61 L, Q61R, and/or Q61K in codon 61; and/or A146T in codon 146 mutations. In some embodiments, the first domain is for detection of at least one single mutation in an NRAS oncogene. In some embodiments, the first domain is for detection of at least one NRAS oncogene mutation at codon 12 and/or 13. In some embodiments, the first domain is for detection of at least one NRAS oncogene mutation which includes at least one of G12A, G12C, G12D, G12S, G12V in codon 12, and/or G13D, G13R, G13V in codon 13 mutations. In some embodiments, the first domain is for the detection of at least one single mutation in a BRAF oncogene. In some embodiments, the first domain is for the detection of at least one BRAF mutation at codon 600. In some embodiments, the first domain is for the detection of one BRAF oncogene mutation which is the V600 E in codon 600 mutation. In some embodiments, the first domain is for the detection of at least one single mutation in a PIK3CA oncogene. In some embodiments, the first domain is for the detection of at least one PIK3CA mutation at codon 542, 545, and/or 1047. In some embodiments, the first domain is for the detection of at least one PIK3CA mutation which includes at least one of E542K in codon 542 mutation, E545K in codon 545 mutation, and H1047R in codon 1047 mutation. In some embodiments, the ratio of the first domain to the second domain is about 10:1 to 1:10. In some embodiments, the ratio of the first domain to the second domain is about 10:1 to 1:1. In some embodiments, the composition comprises at least two of the reporter molecules, which are different, and at least one solvent for the two different reporter molecules.

Other embodiments provide for an assay comprising the step of hybridization using the reporter molecule as described and/or claimed herein. Other embodiments provide for a method of making the reporter molecule as described and/or claimed herein comprising surface functionalizing the core with the first domain and the second domain. Other embodiments provide for a kit comprising the reporter molecule as described and/or claimed herein.

In some preferred embodiments, which are described in more detail hereinafter, an oligonucleotide microarray is described combined with in-tube specific hybridization between single stranded tagged-PCR products and specific dual-domain oligonucleotide reporters that direct the hybridized single stranded DNA to specific points on the surface of a microarray. In preferred embodiments, the tagged-PCR captured on the microarray can be revealed by a fluorescent, universal oligonucleotide. With this multiplex system, one is able in preferred embodiments to correctly genotype, for example, the 7 most frequent codon 12 and/or 13KRAS mutations in tumor biopsies with high sensitivity (e.g., less than 0.1% of mutant DNA). The results show that, in preferred embodiments, this method is suitable for routine diagnosis of disease in clinical practice, e.g., cancer in tissue biopsy or in liquid biopsy ("liquid biopsy" describes an emerging class of blood tests meant to replace tissue biopsy for obtaining diagnostic, prognostic, and theranostic information concerning cancer noninvasively). The potentialities of the method are demonstrated using as a preferred system the KRAS genotyping, but this method can be applicable to other clinical settings.

One or more additional advantages can be derived from or inherently present in the disclosure provided herein.

BRIEF DESCRIPTION OF THE FIGURES

FIG. 1. Assay scheme. (A) A single strand PCR product, encompassing a SNP region, is hybridized with two oligonucleotides called "reporters" whose sequence consists of two parts (domains), one complementary to the potentially mutated sequence of the gene, and the other complementary to an oligonucleotide immobilized on the surface of a microarray slide, called "barcode." The mutated and wild type reporters are associated to two different barcode sequences. In the hybridization conditions used, only the reporter fully complementary to the PCR product (wild type or mutated) forms a hybrid. In the case of FIG. 1, the sample contains only a KRAS wild-type allele, therefore only the specific wild-type reporter hybridizes in solution with the single strand PCR product (ssPCR), whereas the specific mutant reporter (with the variant position circled and in red) does not. FIG. 1(A) discloses SEQ ID NO: 10.

After hybridization has occurred, the solution contacts a microarray surface where oligonucleotides complementary to the barcode sequences are spotted at specific locations. As shown in FIG. 1(B), different barcodes in the 3' portion of the reporter sequences (Barcode W for wild-type allele, Barcode M for mutated allele) capture their complementary sequences. However, only the barcode sequence that is bound to the reporter that has formed a hybrid with the PCR becomes fluorescent as, only the PCR fragment is tagged at 5'-end with a sequence, called U-TAG, that interacts with the complementary Cy3-labeled oligonucleotide, Universal-Cy3 (U-Cy3), added in the last step of the assay. FIG. 1(B) discloses SEQ ID NO: 10.

FIG. 2. Representative sequence of operation steps, with time needed for the steps, in the assay. The total time is 87 minutes.

FIG. 3. Fluorescent images of eight microarray slides, each spotted with eight barcode sequences (one for wild type and seven for the mutated sequences) for the genotyping the seven (G12A, G12C, G12D, G12R, G125, G12V and G13D), more frequent, KRAS mutations This experiment aims to demonstrate that each mutated sequence is captured at a specific location of the array and that there is no cross-talk with other barcode sequences.

(A) Schematic representation of the spotted barcode probe array. Silicon chips coated with copoly(DMA-NAS-MAPS) are used as substrates for the covalent attachment of amino-modified barcode probe oligonucleotides spotted at discrete locations. Each position in the 2×4 grid identifies an individual barcode probe address (and corresponding KRAS mutation or wild-type sequence).

(B) Each slide was hybridized with a single strand PCR fragment either wild type or mutated, previously incubated in solution with all the eight different reporters. The barcode associated to the specific reporter drive the construct to the correct position on the array surface. The fluorescence detection was obtained incubating the array with a universal Cy3 labeled oligonucleotide complementary to the tagged-reverse primer of the single strand PCR. G12A, C, D, R, S, V and G13D correspond to the control sample containing the indicated mutation. All the eight samples of known genotype (wild-type or mutated) were correctly identified.

Figure 4:
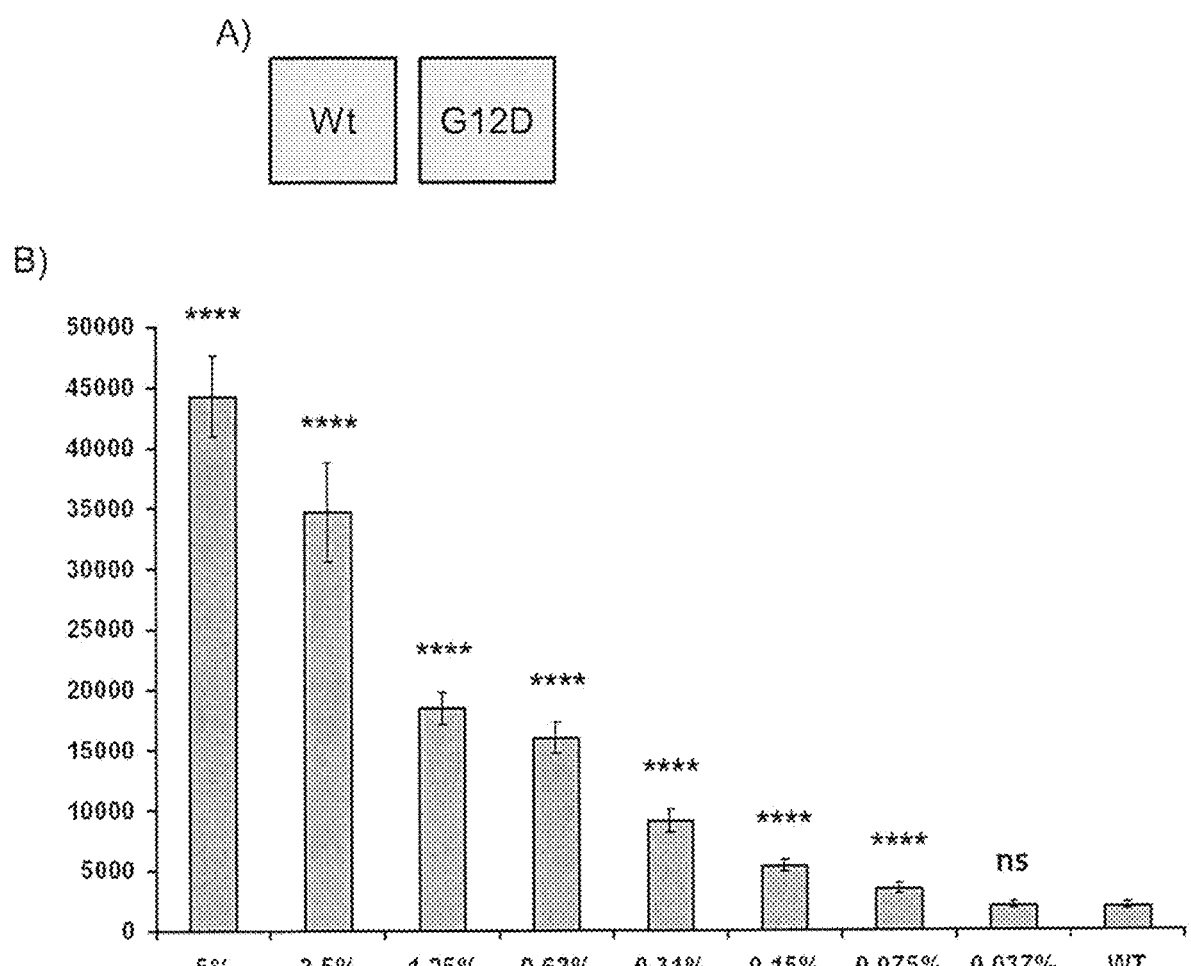

FIG. 4. Detection limit of the G12D KRAS mutation. The sensitivity of the system was evaluated with serial dilution (5%; 2.5%; 1.25%; 0.62%; 0.31%; 0.075%; 0.037%) of mutated DNA opportunely mixed with wild-type DNA.

(A) Schematic representation of the spotted barcode probe arrays for the sensitivity assay. Wt=barcode probe oligonucleotide address for wild-type single strand PCR; G12D=barcode probe oligonucleotide address for G12D KRAS mutation single strand PCR.

(B) The graph represents the relative fluorescence intensity of the signal corresponding to the Cy3-labeled mutated single strand PCR bound to the G12D barcode probe. The fluorescence intensity of the signal corresponding to the Cy3-labeled wild-type single strand PCR bound to the wild-type barcode probe is not shown to simplify the histogram. All the bars are the average of the intensity of the 36 spots (6×6 sub-array) of the G12D barcode probe array. WT=background fluorescence presents on the G12D barcode probe array of the chip hybridized with wild-type control sample. The error bars are the standard deviations of the fluorescence intensity of each sample. The stars represent the results of unpaired t Test for the different dilution curve points respect to the WT control. ns=not significant. Significant: $p<0.05$; *=$p<0.05$; =$p<0.01$; *=$p<0.001$; ****=$p<0.0001$.

Figure 5:
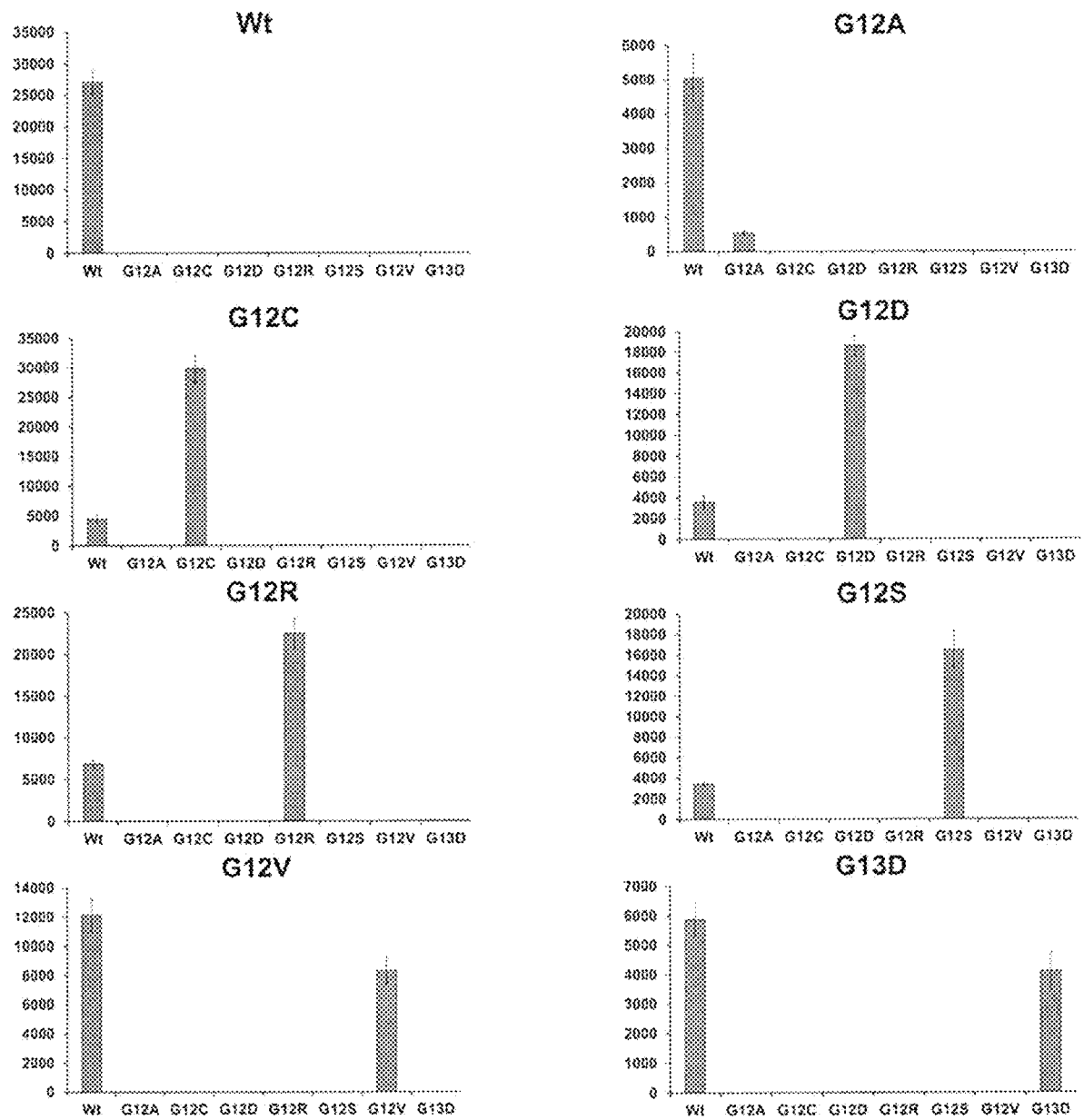

FIG. 5. Genotyping of the KRAS mutations in Formalin-Fixed Paraffin-Embedded (FFPE) samples. The spotting scheme of the barcode sequences is the same of FIG. 3A. The plots of the relative fluorescence intensity after hybridization of eight control clinical samples with eight spotted chips are represented. G12A, C, D, R, S, V and G13D indicate the FFEP genotype. All the bars are the average of the intensity of the 36 spots (6×6 sub-array) of each barcode probe sub-arrays. The error bars are the standard deviations of the fluorescence intensity of each sample.

Figure 6:
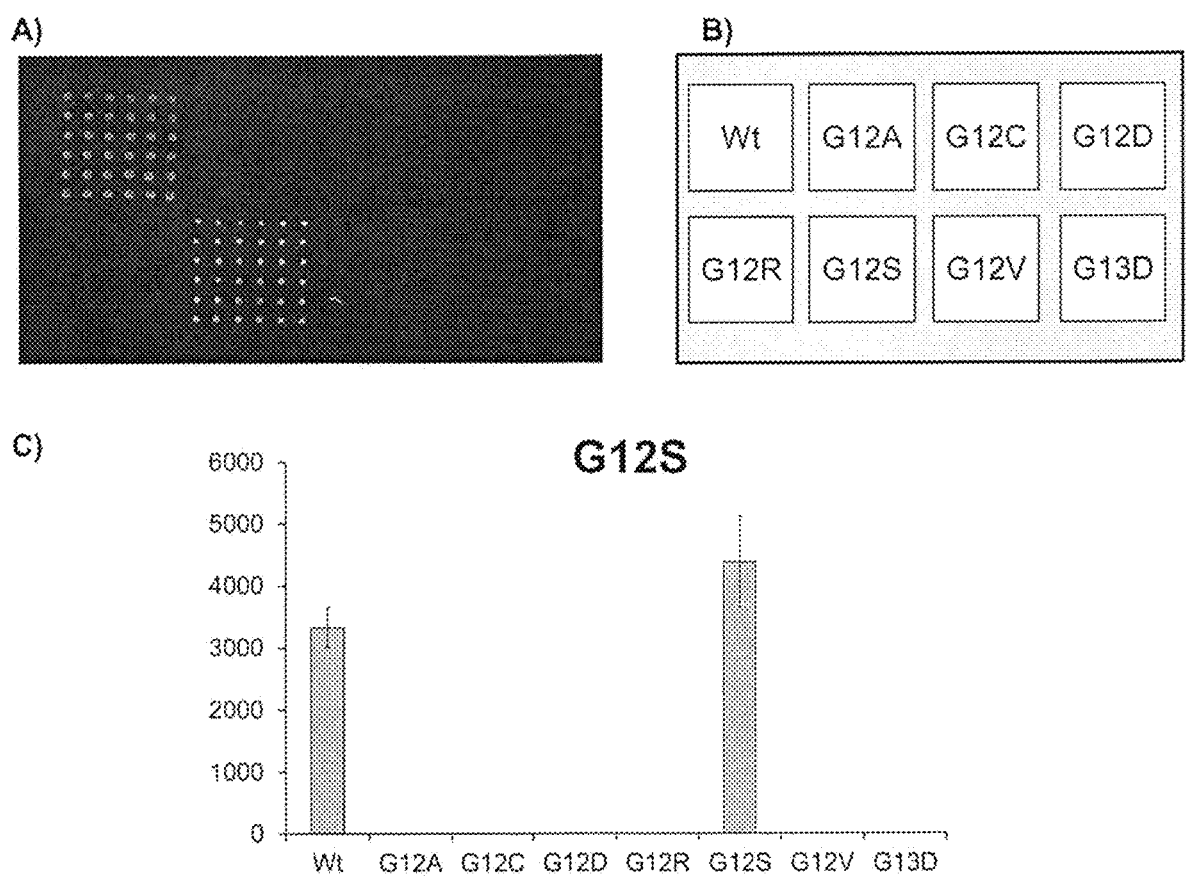

FIG. 6. Microarray image for the analysis of the G125 mutation sample. (A) Cy3 fluorescence image obtained after hybridization of the single strand PCR-reporters complex with the universal tag-array. Universal means that all mutated or wild type PCR fragments are detected with the same oligonucleotide. (B) Schematic representation of the spotted barcode sequences. Each position in the 2×4 grid identifies an individual barcode probe address (and corresponding KRAS mutation or wild-type sequence). (C) The plot of the relative fluorescence intensity. All the bars are the average of the intensity of the 36 spots (6×6 sub-array) of each barcode probe sub-arrays. The error bars are the standard deviations of the fluorescence intensity of each sample.

In FIGS. 7-11, for sub-embodiments, the two parts of the reporter molecule are bound to a core structure such as a synthetic polymer or a macromolecular scaffold. This increase the number of reporters and barcodes on the reporter molecule and can increase sensitivity.

Figure 7:
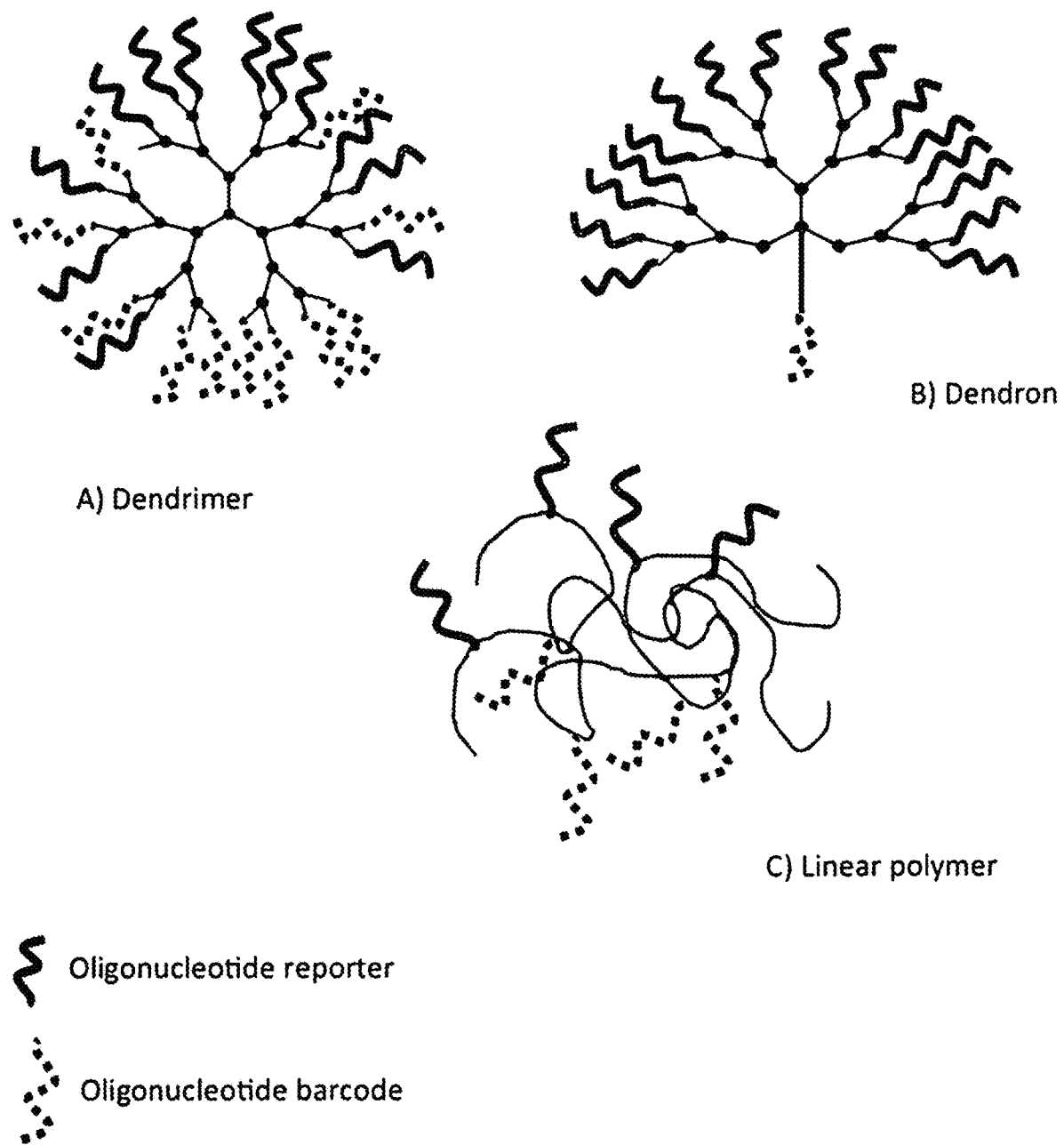

FIG. 7. Examples of polymeric, or macromolecular, scaffolds (cores) bound to reporter and barcode sequences of reporter molecules including dendrimer core, Dendron core, and linear polymer core. The cores are surface functionalized.

Figure 8:
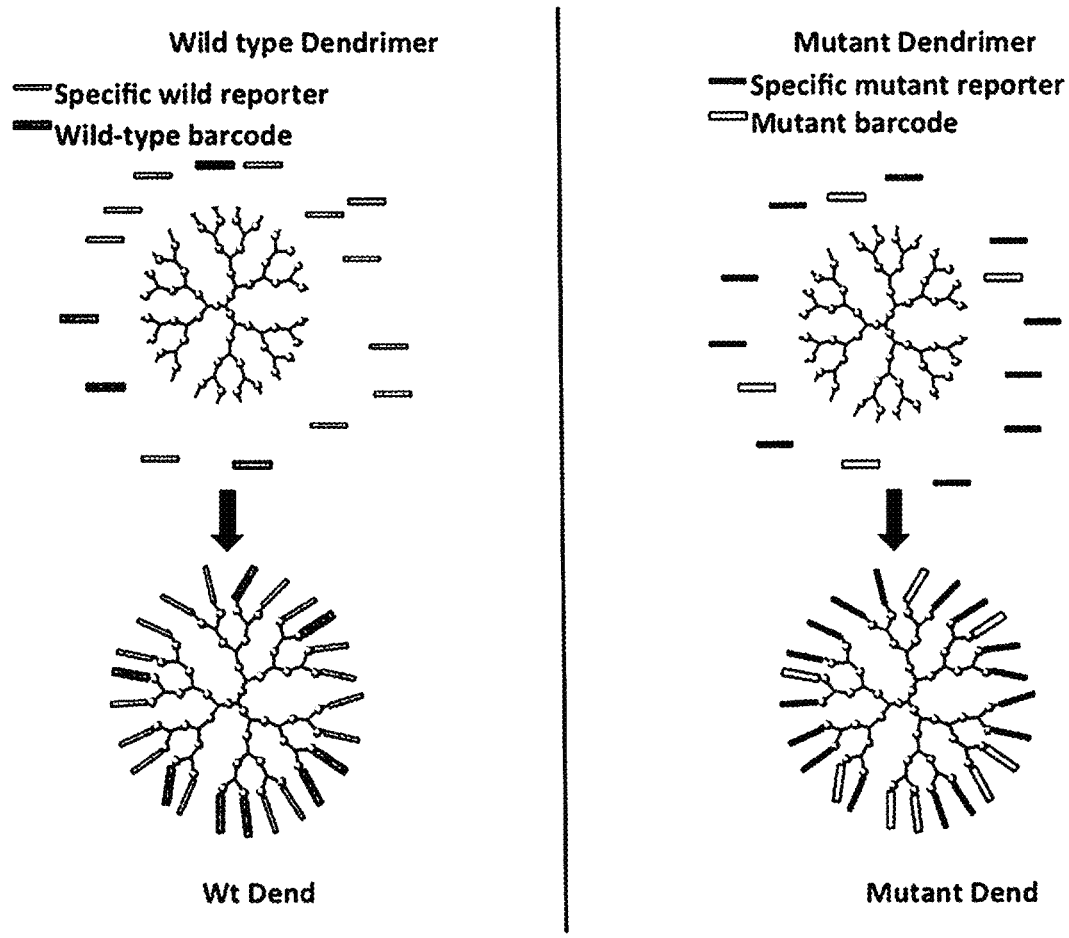

FIG. 8. Scheme of azido dendrimer derivatization: DBCO modified oligonucleotides are added to a solution of azido dendrimer. In particular the oligonucleotide complementary to the PCR (wild type or mutant barcode) is 4 fold the oligonucleotide complementary to the spotted probe (specific reporter).

Figure 9:
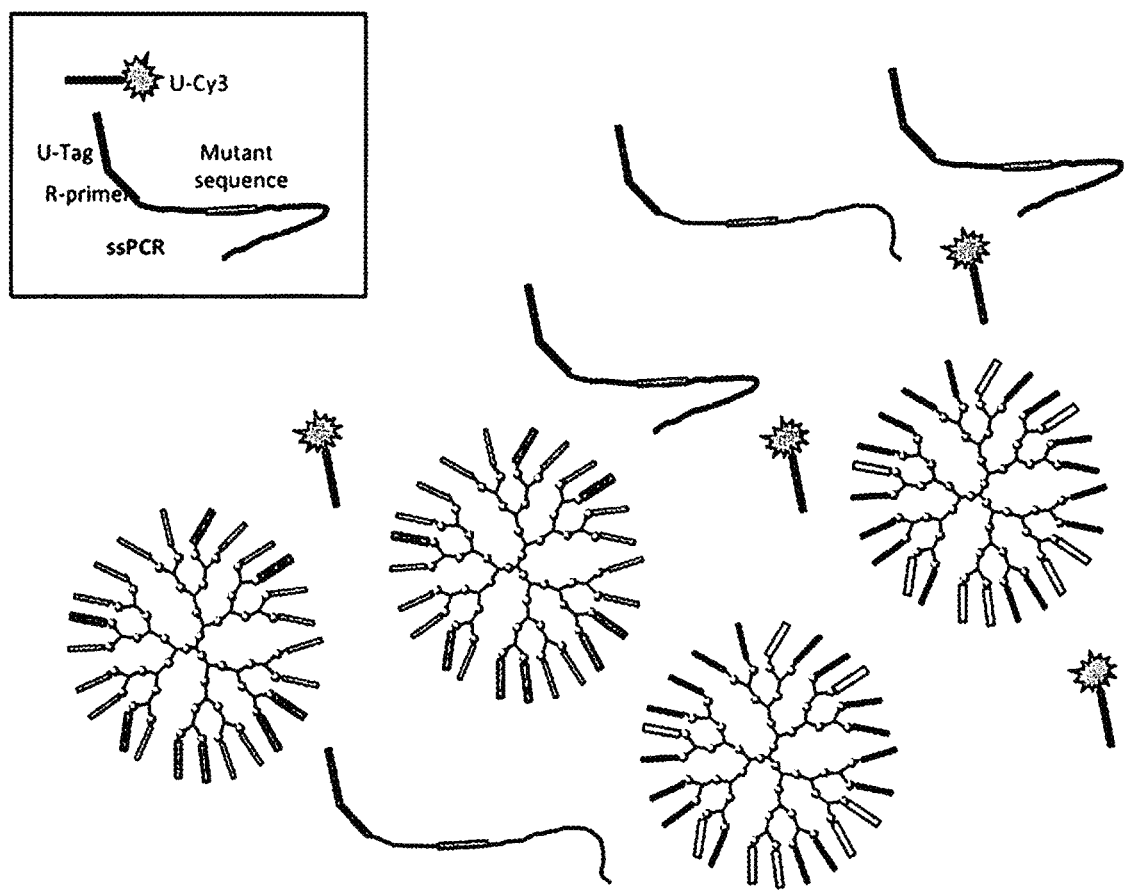

FIG. 9. Scheme of mutant PCR hybridization to the dendrimer modified with sequences complementary to the mutant sequence of the PCR.

Figure 10:
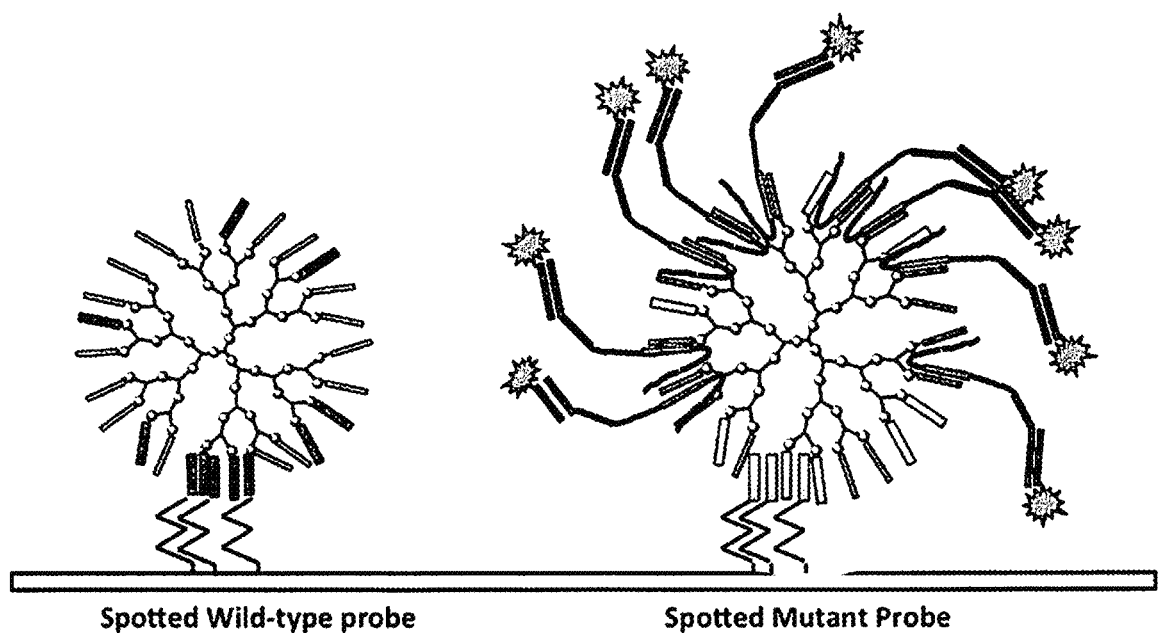

FIG. 10. The azido dendrimer modified with mutant oligonucleotides hybridizes with the mutant PCR and recognizes the mutant probe on the surface.

Figure 11:
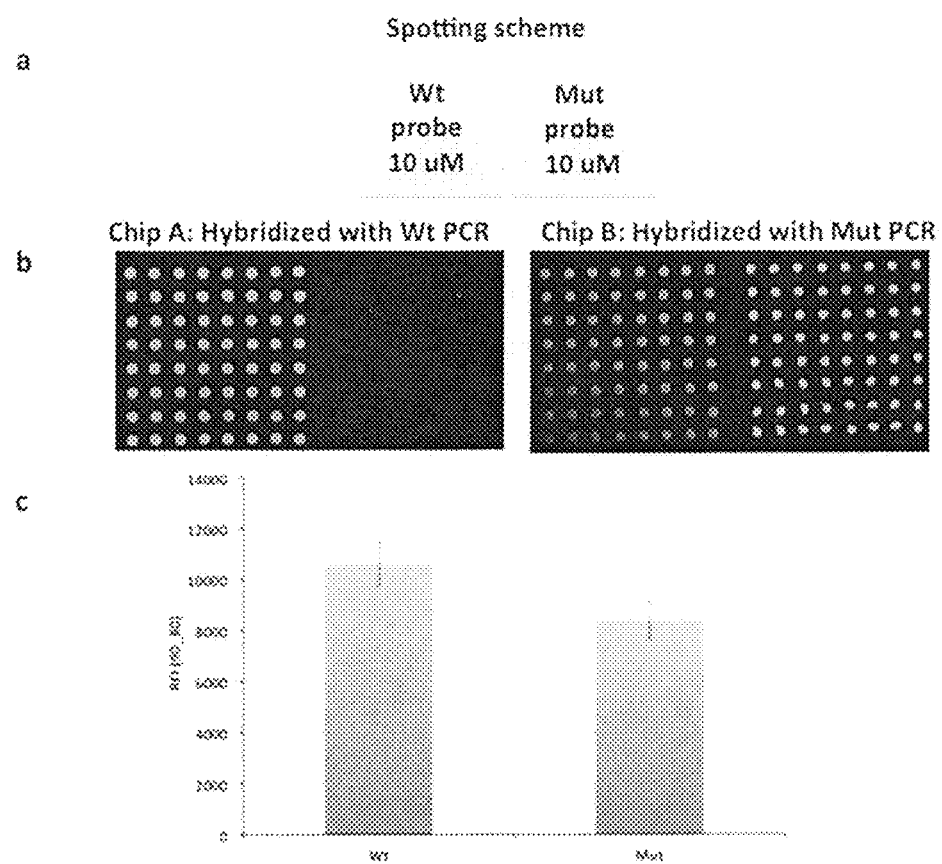

FIG. 11. (a) Spotting scheme: both the wild type (left array) and mutant barcode probes (right array) are spotted on each chip at 10 µM in 150 mM sodium phosphate pH 8.5, 0.01% Sucrose monolaurate (b) fluorescence image after hybridization with dendrimers modified with Wt PCR (chip A) and dendrimer modified with Mut PCR (ChipB) and (c) fluorescence intensity signals.

Figure 12:
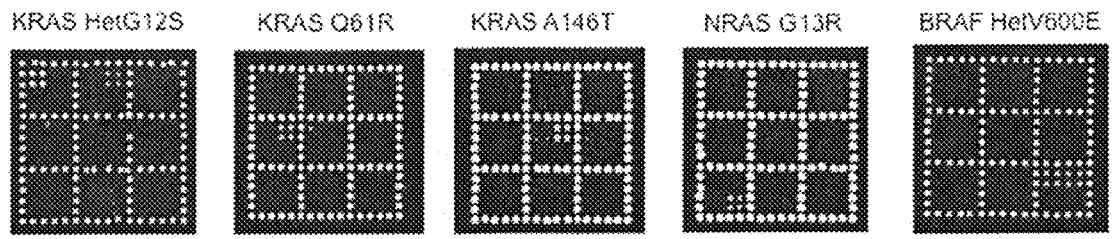

FIG. 12. Expanded set of sequences: (A) Schematic representation of the spotted barcode probe array. (B) Microarray scanning of the Cy3 fluorescence signal of five different silicon chips.

Figure 13:
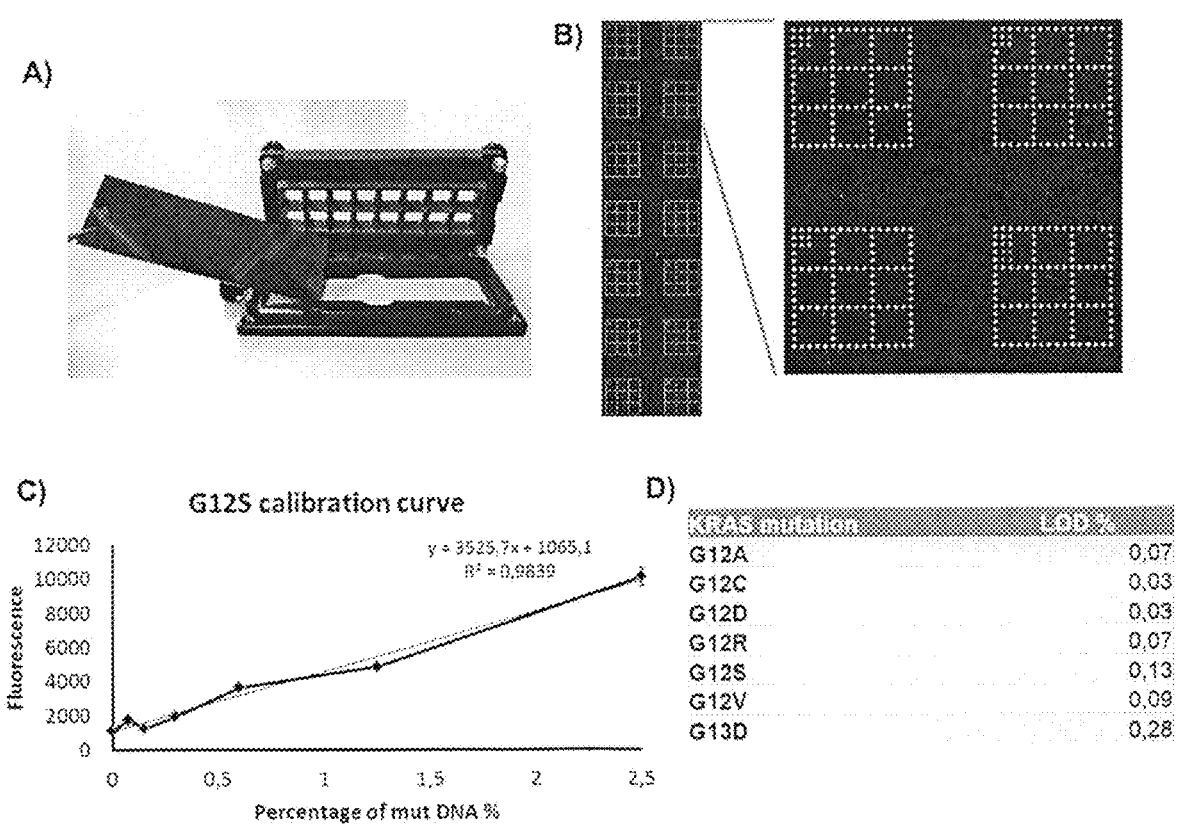
Figure 14:
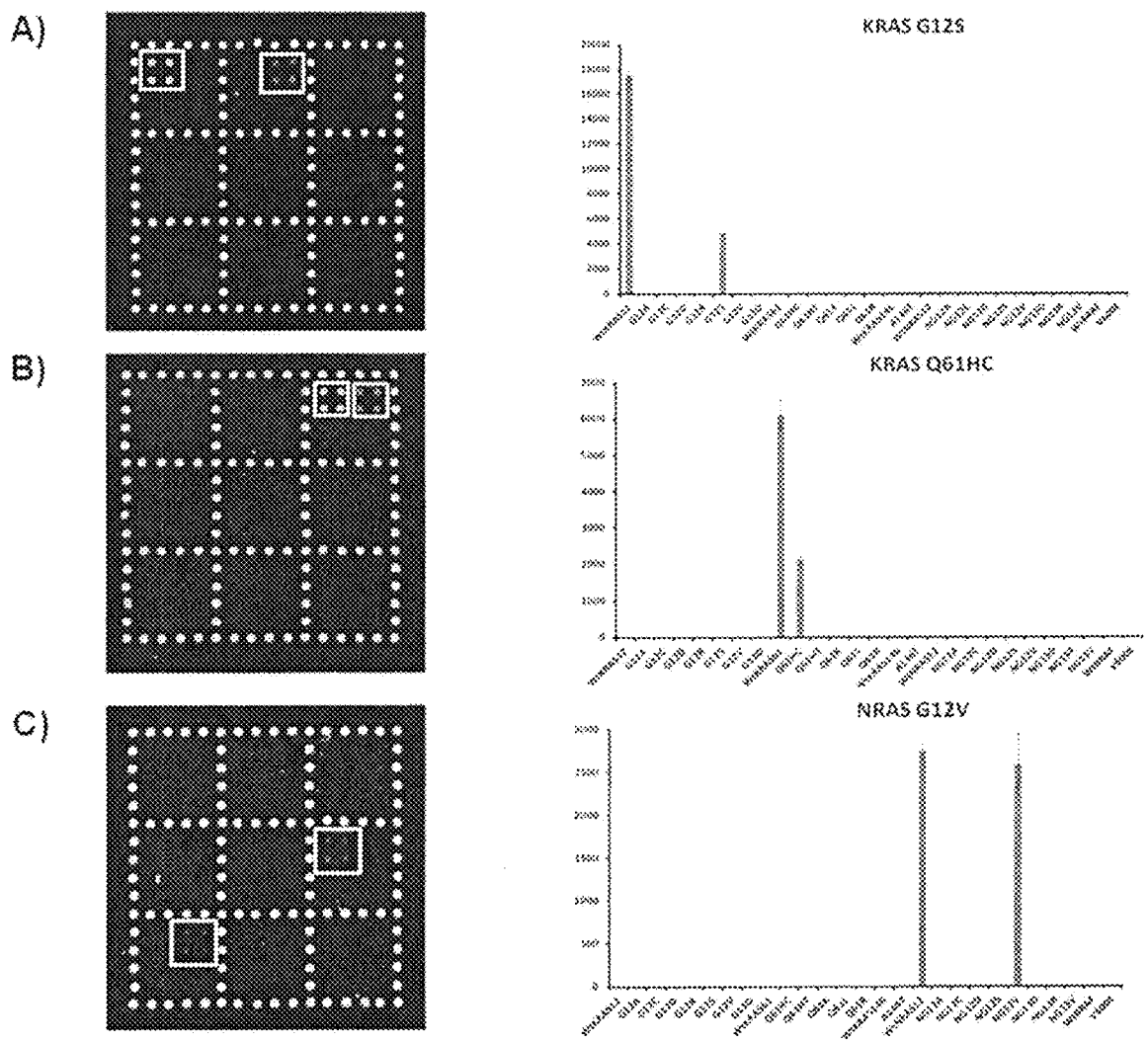

FIG. 13. Showing lower detection limits: using a 16-well incubation chamber, mixtures of wild type and mutated DNA in different ratios were incubated in parallel on different wells of the same slide (A) and (B). (C) shows an example of calibration curve for the KRAS G12S mutation. The table (D) reports the limit of detection for each mutation FIG. 14. To evaluate the applicability of the tag-microarray approach in a real clinical setting. FFPE samples were analyzed. Typical results are shown in FIG. 14 for the samples identified with (A) KRAS G12S, (B) KRAS Q61HC mutations, and (C) NRAS G12V mutation.

Figure 15:
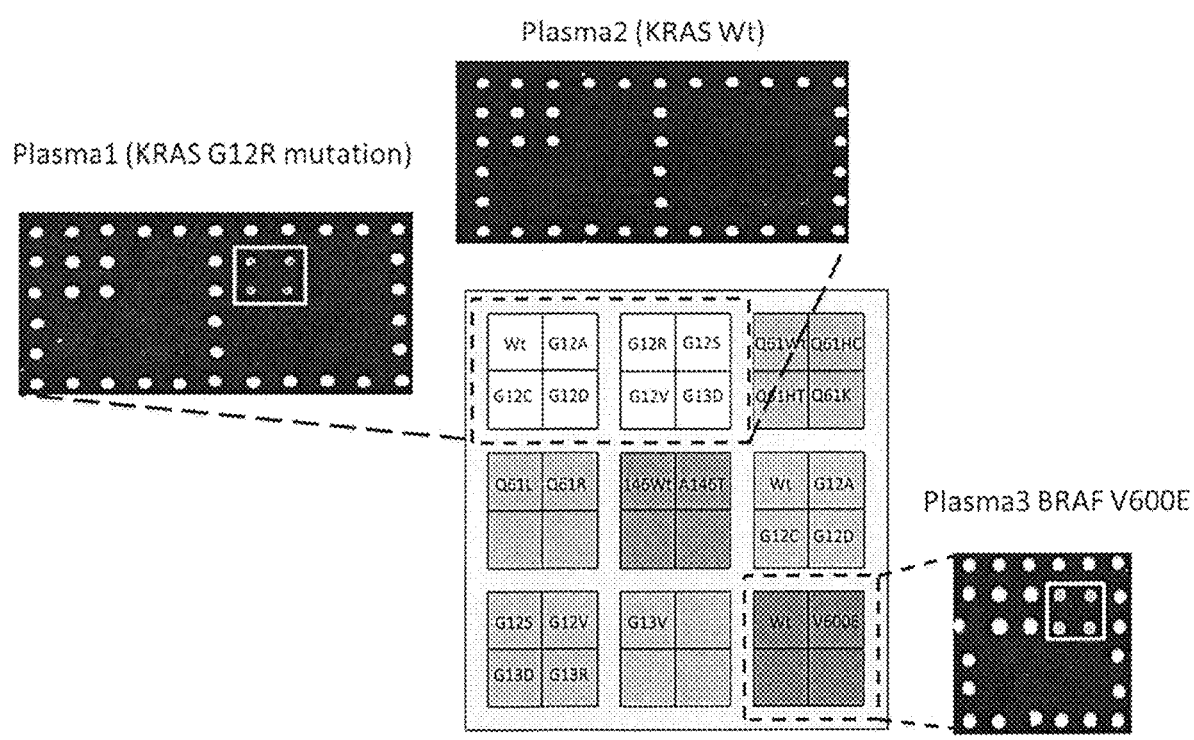

FIG. 15. To evaluate the applicability of the tag-microarray approach in liquid biopsies, 3 ctDNA samples were analyzed. The array was used in a liquid biopsy to analyze cell-free circulating tumor DNAs (ctDNA) from plasma extracted from patients with colorectal cancer, and the results of the microarray analysis are shown in FIG. 15, and their correctness was confirmed with droplet digital PCR.

The figure shows a typical fluorescence image of the array used to detect one of the 22 mutations reported in the scheme. ctDNA of three patients, two mutated and one wild type are analyzed. While the wild type signals is always present (top left), only mutated DNA generate the signals in the yellow squares. From the intensity of these signals the concentration of mutated DNA can be assessed through a calibration curve.

APPENDED TABLES

Table 1. Sequences of spotted probes (SEQ ID NOS 11-18, 29-34, and 43-44, respectively in order of appearance) and reporters (SEQ ID NOS 19-26, 35-40, and 45-46, respectively in order of appearance) for KRAS mutations. SEQ ID NOS 27-28, 41-42, and 47 are also disclosed, respectively, in order of appearance.

Table 2. Sequences of spotted probes (SEQ ID NOS 48-49, respectively in order of appearance) and reporters (SEQ ID NOS 50-51, respectively in order of appearance) for BRAF mutations. SEQ ID NOS 52-53 are also disclosed, respectively, in order of appearance.

Table 3. Sequences of spotted probes (SEQ ID NOS 54-55, 59-60, and 64-65, respectively in order of appearance) and reporters (SEQ ID NOS 56-57, 61-62, and 66-67, respectively in order of appearance) for PIK3CA mutations. SEQ ID NOS 58, 63, and 68-69 are also disclosed, respectively, in order of appearance.

Table 4. Sequences of spotted probes (SEQ ID NOS 70-78, respectively in order of appearance) and reporters (SEQ ID NOS 79-87, respectively in order of appearance) for NRAS mutations. SEQ ID NO: 88 is also disclosed.

DETAILED DESCRIPTION

Introduction

Additional embodiments are provided in the following detailed description, including working examples.

US priority provisional application, U.S. Ser. No. 62/479, 995 filed Mar. 31, 2017, is hereby incorporated by reference in its entirety for all purposes.

A listing of cited references is provided later in this document. No admission is made that any of these references, or any other references cited in this document, are in fact prior art.

The present description includes, as supported by existing law, all transitional phrases, whether open or closed, including "comprising," "consisting essentially of," and "consisting of," and including if used in a claim preamble or for a particular element of a claim. Hence, for example, if an embodiment is described and/or claimed with use of "comprising," the embodiment also can be written with replacement of "comprising" with "consisting essentially of" or "consisting of." With respect to "consisting essentially of," this phrase limits the scope of a claim or an element to the specified materials or steps "and those that do not materially affect the basic and novel characteristic(s)" of the claimed invention or element.

In a preferred embodiment, PCR/LDR (polymerase chain reaction/ligase detection reaction) steps are not used in the assay (see, for example, Favis et al., *Annals New York Academy of Sciences*, 906, 39-43 (2000) for PCR/LDR). In a preferred embodiment, an enzyme is not used in the assay. In a preferred embodiment, the reporter molecule is not immobilized on a surface.

Fundamentals of nucleic acids and genome science are known in the art. See, for example, Calladine et al., *Under-*

*standing DNA, The Molecule and How it Works, Second Edition*, 1997; Gibson et al., *A Primer of Genome Science*, 2002. For genotyping and microarrays in the patent literature, see, for example, WO 2011/080068; WO 01/21838; WO 00/61801; WO/65098; WO 01/25485; WO 98/28438; and US Pat. Pub. 2005/0244860. This includes knowledge about single stranded and double stranded DNA, oligonucleotides, isolation of nucleic acid molecules and polymers from cells, and complimentary sequences which are able to hybridize to each other.

A wide variety of genetic sources can be studied by the assay methods described herein including human genetic sources (tissues taken from humans or cell-free circulating DNA extracted from plasma). The assays can be part of disease diagnostics, disease prediction, disease prophylactic and prevention steps, and disease therapies and cures. The humans (and tissues taken from humans) which are subjected to the assay can be either already diagnosed with a disease or not yet diagnosed with a disease. A preferred target for the inventive assay is human cancer and application to DNA extracted from tissues removed from human cancer patients or circulating in blood. Of course, the assays can be used more generally with animals and their diseases if desired.

Fives steps in the assay are described more below including the amplifying step, the isolating step, the hybridization step, the contacting step, and the detection step. Steps in larger assay methods such as hybridizing, contacting, and detecting are known in the art (e.g., see U.S. Pat. No. 6,806,047)

Figure 2:
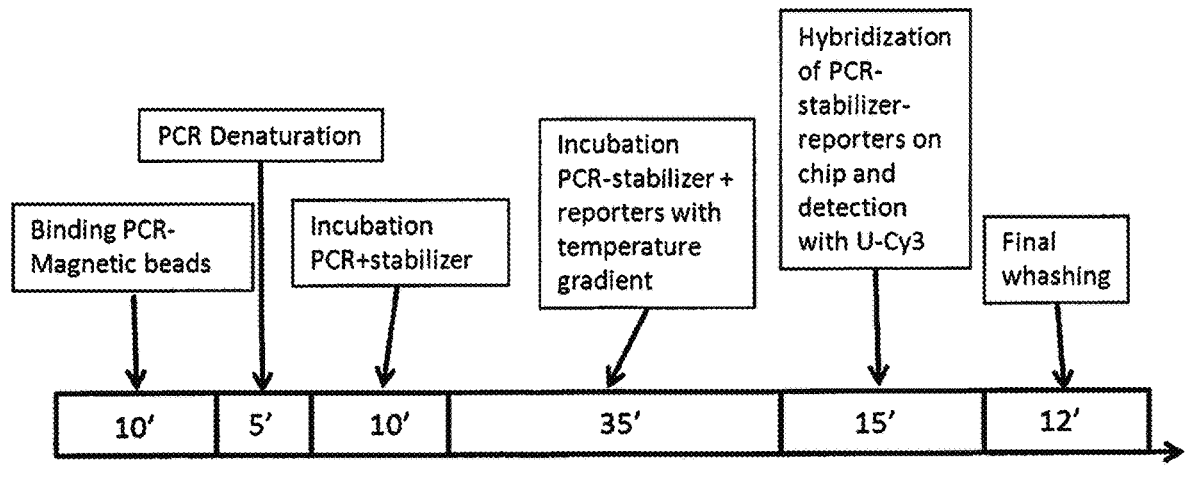

FIG. 2 illustrates an embodiment which shows a sequence of steps which follow amplification of the fragment of interest. These include: (1) capturing of PCR-magnetic beads, (2) PCR denaturation, (3) incubation of PCR and stabilizer, (4) incubation of PCR-stabilizer and reporters in temperature gradient, (5) hybridization of PCR-stabilizer-reporters on chip and detection with U-Cy3, and (6) final washing step.

One aspect provides for an assay method for a gene fragment of interest comprising:

amplify at least one gene fragment of interest encompassing at least one SNP region of interest to form an initial amplification product, wherein the fragment to be amplified is primed in the amplification to enable (1) isolation of one single strand from another single strand of the initial amplification product in a later step of the assay, and (2) detection of the isolated single strand in a later step in the assay;

isolate at least one single strand amplification product from the initial amplification product, wherein the single strand amplification product either contains or potentially contains the at least one SNP region of interest;

hybridize in solution the single strand amplification product with at least one reporter molecule which comprises at least two, different domains of oligonucleotide, wherein a first domain of oligonucleotide is for hybridization with the single strand amplification product, and wherein the second domain of oligonucleotide is for hybridization to at least one microarray probe surface, wherein the microarray probe surface comprises at least one capture probe to allow for hybridization;

contact the solution of the hybridized single strand amplification product with the at least one microarray probe surface which comprises at least one capture probe to allow for hybridization;

detect for the presence of the hybridized single strand amplification product on the microarray surface.

A more specific aspect is an assay method for a KRAS, NRAS, BRAF, and/or PIK3CA oncogene fragment of interest comprising:

amplify at least one KRAS, NRAS, BRAF, and/or PIK3CA oncogene fragment of interest comprising or potentially comprising at least one SNP region of interest to form an initial amplification product, wherein the fragment to be amplified is primed in the amplification to enable (1) isolation of one single strand from another single strand of the initial amplification product by coupling to a bead in a later step of the assay, and (2) detection of the isolated single strand by fluorescent detection in a later step in the assay;

isolate at least one single strand amplification product from the initial amplification product with use of denaturation and coupling to a bead, wherein the single strand amplification product either comprises or potentially comprises the at least one SNP region of interest, wherein optionally the isolated single strand amplification product is stabilized before further hybridization;

hybridize in solution the single strand amplification product with at least one reporter molecule which comprises at least two, different domains of oligonucleotide, wherein a first domain of oligonucleotide is for hybridization with the single strand amplification product, and wherein the second domain of oligonucleotide is for hybridization to at least one microarray probe surface, and wherein the hybridization step comprises application of a temperature gradient covering at least two different hybridization temperatures, and wherein the microarray probe surface comprises at least one capture probe to allow for hybridization;

contact the solution of the hybridized single strand amplification product with the at least one microarray probe surface which comprises at least one capture probe to allow for hybridization;

detect with fluorescence for the presence of the hybridized single strand amplification product on the microarray surface.

Additional embodiments are described in more detail below.

The Amplification Step

Amplification methods for gene fragments are known in the art, particularly PCR amplification. Amplification can be carried out with either single strand or double strand nucleic acids. Also known is the manipulation and sequencing of amplification products. See, for example, Bevan et al., "Sequencing of PCR-amplified DNA," *PCR Methods and Applications*, pages 222-228 (1992); T. A. Brown, *Gene Cloning and DNA Analysis: An Introduction* 7th Edition, 2016, including descriptions of PCR.

A broad range of gene fragments of interest can be used, and the KRAS, BRAF, PIK3CA, and NRAS genes are preferred embodiments. The amplification step, as known in the art, can produce an "initial amplification product." This initial amplification product then can be converted into a single strand amplification product which is subjected to further assay steps. The number of base pairs in the fragment to be amplified is not particularly limited but can be, for example, 50 bp to 300 bp, or 100 bp to 200 bp.

"Gene fragments of interest" are known in the art and can include or potentially include one or more SNPs and/or SNP regions as known in the art.

The gene fragment of interest can be "primed" as known in the art in forming the initial amplification product. Forward primers and reverse primers are known in the art. The priming can be done in a way so that the fragment to be amplified is primed in the amplification to provide for (1) isolation of one single strand from another single strand of the initial amplification product in a later step of the assay, and (2) detection of the isolated single strand in a later step in the assay.

For example, priming can be carried out with use of primers which are part of a specific binding pair for affinity capture as known in the art such as, for example, biotin and streptavidin.

The priming also can be carried out so that the product can be tagged with moieties which allow for detection.

In some embodiments, the assay and the gene fragment of interest are for the detection of at least one single mutation in a KRAS, NRAS, BRAF, and/or PIK3CA oncogene. In some embodiments, the assay and the gene fragment of interest are for the detection of at least one single mutation in a KRAS oncogene. In some embodiments, the assay and the gene fragment of interest are for the detection of at least one KRAS oncogene mutation at codon 12, and/or codon 13, and/or codon 61, and/or codon 146. In some embodiments, the assay and the gene fragment of interest are for the detection of at least one KRAS oncogene mutation at codon 12 and/or codon 13. In some embodiments, the assay and the gene fragment of interest are for detection of at least one KRAS oncogene mutation which includes at least one of G12A, G12C, G12D, G12R, G12S, and/or G12V in codon 12; and/or G13D in codon 13; and/or Q61HC Q61HT, Q61 L, Q61R, and/or Q61K in codon 61; and/or A146T in codon 146 mutations. In some embodiments, the assay and the gene fragment of interest are for the detection of at least one single mutation in an NRAS oncogene. In some embodiments, the assay and the gene fragment of interest are for detection of at least one NRAS oncogene mutation at codon 12 and/or codon 13. In some embodiments, the assay and the gene fragment of interest are for detection of at least one NRAS oncogene mutation which includes at least one of G12A, G12C, G12D, G12S, G12V in codon 12, and/or G13D, G13R, G13V in codon 13 mutations. In some embodiments, the assay and the gene fragment of interest are for the detection of at least one single mutation in a BRAF oncogene. In some embodiments, the assay and the gene fragment of interest are for the detection of at least one BRAF mutation at codon 600. In some embodiments, the assay and the gene fragment of interest are for the detection of one BRAF oncogene mutation which is the V600 E in codon 600 mutation. In some embodiments, the assay and the gene fragment of interest are for the detection of at least one single mutation in a PIK3CA oncogene. In some embodiments, the assay and the gene fragment of interest are for the detection of at least one PIK3CA mutation at codon 542, 545, and/or 1047. In some embodiments, the assay and the gene fragment of interest are for the detection of at least one PIK3CA mutation which includes at least one of E542K in codon 542 mutation, E545K in codon 545 mutation, and/or H1047R in codon 1047 mutation.

One genes, oncogenes, SNPs, and/or mutations can be tested for as known to those skilled in the art.

In some embodiments, the initial amplification product is linked to, for example, a particle or bead, such as a magnetic bead, to enable the isolation of one single strand from another single strand of the initial amplification product in a later step of the assay. In some embodiments, the initial amplification product is linked to a tag which enables, for example, fluorescent detection of the isolated single strand in a later step in the assay. In some embodiments, the amplification step comprises PCR amplification.

The Isolation Step

In some embodiments, an isolation step can be carried out. In such embodiments, the initial amplification product can be then subjected to an isolation step in which a single strand amplification product is isolated and the other single strand can be discarded or used for other purposes. For example, using affinity capture and specific binding, the one strand can be bound to a solid phase such as a particle, including a magnetic particle. After binding, the bound strand can be separated from the single strand of interest for further use in the assay.

In some embodiments, the isolation step comprises thermal denaturation of the initial amplification product and separation of the one single strand from the other single strand. In some embodiments, the hybridization step comprises application of a temperature gradient covering at least two different hybridization temperatures. In some embodiments, the hybridization step comprises hybridization of wild-type sequences. In some embodiments, isolated single strand amplification product is stabilized before further hybridization.

One embodiment provides for an amplification product which is combined with a bead or particle and is separated by, for example, centrifugation.

In other embodiments, the isolation step is not carried out.

The Hybridization Step

The single strand amplification product, which has been appropriately primed and isolated (purified), is then subject to a hybridization step with at least one reporter molecule in solution. The reporter molecule comprises at least two, different domains of oligonucleotide, wherein a first domain of oligonucleotide is for hybridization with the single strand amplification product, and wherein the second domain of oligonucleotide is for hybridization to at least one microarray probe surface. One reporter molecule can include only one first domain and only one second domain. In addition, one reporter molecule can comprise two or more first domains and/or two or more second domains. Sensitivity can be increased by use of more domains per reporter molecule.

Multiple, different reporters can be used. Hence, multiplexing can be carried out, and the number of different reporter molecules is not particularly limited. The number can be, for example, 2, 3, 4, 5, 6, 7, 8, 9, 10, 11, or 12.

In one embodiment, the reporter molecule is a single oligonucleotide which contains the two different domains, the first domain and the second domain. In another embodiment, a carrier or a core is used, wherein the first and second domains are different oligonucleotides linked to the carrier or core. Here, the reporter molecule comprises a macromolecule or polymer which is conjugated to or covalently bonded to the first and second domains. The macromolecule can be, for example, a water soluble polymer, a dendrimer, or a dendron, as described more below. Water soluble polymers, dendrimers, and dendrons are known in the art. The water soluble polymer, dendrimer, and dendron can be highly branched so as to form a core, which can be surface functionalized with the first domain and with the second domain.

Examples of reporter sequences (or domains) are shown in Tables 1-4 for four mutations, including both first domain and the second domain, but other reporter sequences can be used to meet the need. This includes both the sequences which hybridize to single strand amplification product, and also the sequences which are designed to hybridize to the spotted capture probes ("tails of the reporter").

In a preferred embodiment, the hybridization step comprises application of a temperature gradient covering at least two different hybridization temperatures. Temperature gradients used to control hybridization are known in the art (see, for example, US Patent Publication 2005/0221367). The hybridization steps can comprise application of a temperature gradient covering at least two, three, four, five, six, or seven (for example) different hybridization temperatures if more than one oligonucleotide reporter is used. Linear or stepwise gradients can be used. For example, one can use a stepwise gradient leaving the solution at specific temperatures for, for example, 1-20 minutes, or 1-10 minutes, or about five minutes. Table 1 below shows examples of specific hybridization temperatures which can be used for particular sequences, but other hybridization temperatures and sequences can be used. The hybridization temperature can be varied based on factors known in the art such as salt concentration. The hybridization temperature can be any known hybridization temperature. The hybridization temperature can be in a range such as, for example, 25° C. to 65° C., 27° C. to 55° C., 28° C. to 45° C., or 29° C. to 41° C.

In a preferred embodiment, the hybridization step comprises hybridization of wild-type sequences.

In a preferred embodiment, the isolated single strand amplification product is stabilized before hybridization. More particularly, the conformation of the isolated single strand amplification product can be stabilized by hybridization with an oligonucleotide whose sequence is complementary to a region adjacent to the region complementary to the reporter, which can be called a stabilizer. A stabliizer can be an oligonucleotide necessary to open the secondary structures present in the amplicon before further hybridization with the reporter. Tables 1-4 show examples of stabilizer sequences, but other stabilizers can be used.

The Contacting Step

A solution which comprises the hybridized reporter molecule can be then contacted with at least one microarray probe surface which comprises at least one capture probe. Microarrays are generally known in the art. See, for example, Kohane et al., Microarrays for an Integrative Genomics, 2003; Mueller et al., Microarrays, 2006.

The microarray can comprise at least three elements, and these elements can be processed into a microarray by methods known in the art.

A first element, as known in the art, is the solid microarray substrate which can be, for example, made from an inorganic material and can be, for example, a silicon chip or a glass slide.

A second element, as known in the art, is a coating which can be applied to the substrate. The coating can be a thin film coating less than 100 microns thick. The coatings can be based on one or more polymers having multiple repeating units with different functions such as copolymers and terpolymers. The majority of the repeating units can be, for example, acrylamide or methacrylamide monomers. Minority repeating units can allow for further binding. In one function, the coating polymer and its coating layer can covalently bind to one or more biomolecules including capture probes. For example, the coating can have repeat units bearing electrophilic groups (e.g., NAS, N-acryloyloxysuccinimide) which react with nucleophilic groups, such as amino groups. The coating also can have repeat units which are reactive or enable better binding with the substrate surface such as a reactive silane group. Also, after the coating has immobilized the desired biomolecule (e.g., a capture probe), the coating can be "blocked" with a blocking moiety, as known in the art, such as amino compounds, including ethanolamine, so as to eliminate remaining functional groups in the coating which would interfere with the assay and facilitate non-specific binding. Coatings useful for immobilizing biomolecules and coating of substrates for use in arrays are described in, for example, Chiari US patent publications, 2006/0141464; 2013/0115382; 2016/0200847; and 2016/0228842.

A third element is one or more capture probes, usually different capture probes, which are biomolecules adapted to bind to the coating on the substrate and bind and hybridize to moieties in the solution which is contacted with the microarray surface. The capture probes can be used in the form of arrays or dots as known in the art. The capture probes can be applied to the coating by spotting methods known in the art to form the desired pattern and array. The capture probes can be oligonucleotides which are functionalized to react with the coating polymer. The number of capture probes can be adapted to the particular assay.

In another embodiment the capture probe or oligonucleotide is bound to a particle, and the hybridization event is detected by a flow-cytometer of the type used in Luminex system.

The spotted capture probes described in Tables 1-4 are examples only, and other probes can be used to meet the need of the assay.

In some embodiments, the microarray probe surface comprises at least seven different capture probes as well as probes for capturing wild-type moieties.

In some embodiments, the microarray probe surface comprises at least one terpolymer coating on the substrate surface which binds to the capture probe. In some embodiments, the microarray probe surface comprises at least one terpolymer coating on the substrate surface which binds to the capture probe, and which comprises at least one polymer backbone unit which is acrylamide or methacrylamide, at least one second polymer backbone unit which is adapted for binding to the substrate surface, and at least one third polymer backbone unit which binds to the capture probe. In some embodiments, the microarray probe surface comprises at least one terpolymer coating on the substrate surface which binds to the capture probe, and wherein the copolymer is further blocked to prevent non-specific binding during the assay.

The Detection Step

A detection step can be also executed to provide informative information about the gene fragment of interest. The detection can be executed with known methods including, for example, fluorometry, colorimetry, chemiluminescence, or by label free methods through surface plasmon resonance or interferometry. Fluorescent dyes can be used for fluorescent detection, as known in the art.

In some embodiments, the detection step comprises at least one colorimetry, chemiluminescence, label free detection by SPR or interferometry, or fluorescence detection step. Methods known in the art can be used for detection which include, for example, use of a fluorophore, or a particle such as a gold particle, or an enzyme for colorimetric detection. In some embodiments, the detection step is a fluorescence detection step.

Tables 1-4 show an example of a sequence which can be used to bind to the dye, known as Universal-Cy3, but other sequences and dyes can be used. In another embodiment, the universal-tag bears a biotin which can be used to bind, for example, fluorescent streptavidin, streptavidin modified gold particles, or other types of particles.

Kits

One or more kits can be provided for carryout out the inventive assay methods, as known in the art. For example, instructions on use of the kit can be provided. One or more oligonucleotides can be provided as part of the kit. One or more reporter molecules can be provided in the kit. The kit can also be considered a system for carrying out the assay. In one embodiment, a kit is provided which is adapted for carrying out any or all of the assay method steps described and/or claimed herein. Various sub combinations of steps can be carried out with the kit.

Performance and Advantages of the Assay

Many single performance advantages, as well as combinations of performance advantages, are described and demonstrated herein for at least some embodiments.

One particular advantage is the speed or rapidity of the assay. See FIG. 2 and working examples, for example. The assay can be carried out after the amplification step in less than, for example, 240 minutes, or less than 180 minutes, or less than 120 minutes, or less than 90 minutes. There is no particular absolute lower limit on the time as technology advances, better instrumentation and methods are developed, and automation is used. The lower limit can be, for example, 10, 20, or 30 minutes.

Another particular advantage is the sensitivity and detection limit of the assay. See Working Examples and FIG. 4, for example. The detection limit can fall to below 0.1%, or fall to below 0.75%, or fall to below 037%. There is no particular absolute lower limit on the detection limit as technology advances, better instrumentation and methods are developed, and automation is used.

WORKING EXAMPLES

A preferred embodiment is described hereinafter by way of non-limiting working examples.

1. Results 1.1. Overview of the Method

Figure 1:
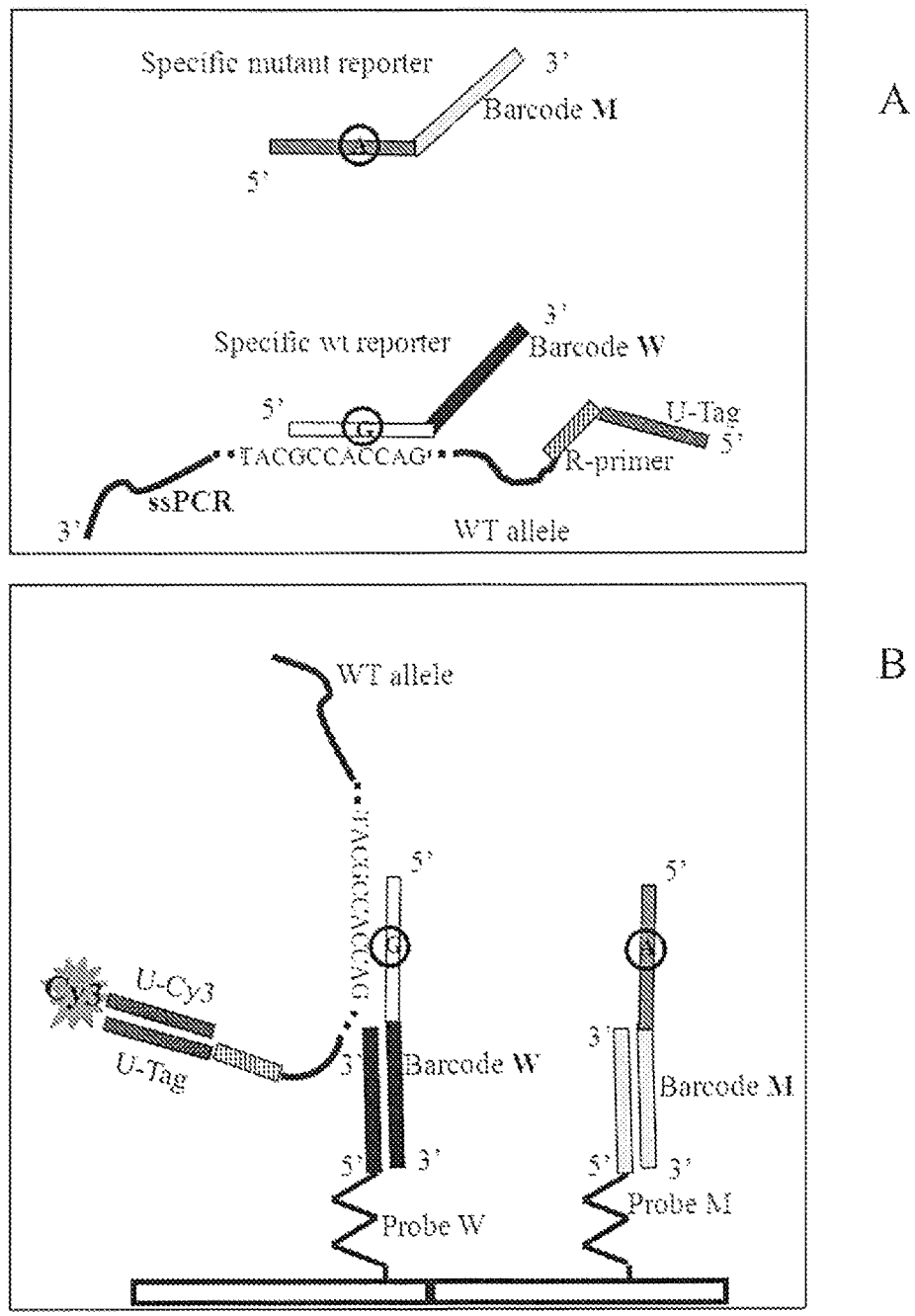
FIGS. 1-15 and Tables 1, 2, 3, and 4 further illustrate preferred embodiments which are described and/or claimed in more detail hereinafter. Any color used in this application as filed, including the filed figures, forms part of the original disclosure and can be relied upon for enablement, written description, and claiming.

The scheme of the assay for a preferred embodiment is shown in FIG. 1. A 167-bp fragment was amplified using 5'-biotin forward and 5'-tagged reverse primers. The biotin allows binding double stranded PCR products to streptavidin-coated magnetic beads, while the tag sequence (Universal-tag, U-tag) on the reverse primers allows detecting single stranded PCR through hybridization with a fluorescent oligonucleotide (Universal-Cy3). After amplification, the biotinylated double stranded PCR product was bound to streptavidin-coated magnetic beads and captured on a magnet. Bead modified PCR fragments were released in solution. Following thermal denaturation, the single strand DNA with the U-tag in the supernatant was recovered while the DNA strand bound to the magnetic beads, was captured with a magnet and discarded. The ssDNA was hybridized in solution with eight specific oligonucleotide reporters whose sequence consists of two domains. The 5' domain corresponds to the KRAS sequence (wild-type or mutant reporters) whereas the 3' domain is a "barcode" sequence that recognizes the oligonucleotide probes spotted at specific locations on the silicon chip (barcode probe). The ssDNA, hybridized with the specific reporters, was captured on the surface of the array through hybridization with the barcode domain. The single strand PCR product, captured at a specific location corresponding to a given mutation, was revealed by incubating the silicon chip with a universal Cy3-oligonucleotide whose sequence is complementary to the U-tag present at the 5'-end of the single stranded PCR.

1.2. Optimization of Genotyping

The Kirstein RAS (KRAS) is the most frequently mutated proto-oncogene that is critical for tumor progression. KRAS mutations occur early in the tumorigenesis pathway, so the detection of KRAS mutations is useful for early diagnosis, prognosis and evaluation of the therapeutic outcome in cancer treatment[29]. KRAS is an effector molecule of epidermal growth factor receptor (EGFR), a key target of therapeutic strategies designed to treat metastatic colorectal cancer (CRC). Constitutively, activating mutations in KRAS at codon 12 or 13 can determine resistance to EGFR-target therapies and patients harboring such mutations do not receive benefit from anti-EGFR treatment. The European health authority (http://www.emea.europa.eu/pdfs/human/press/pr/27923508en.pdf.) as well as the American Society for Clinical Oncology[30] require KRAS mutational analysis on colorectal cancer prior to anti-EGFR therapy. For these evidences it is of great importance to genotype with high accuracy the hot-spot region of KRAS gene.

Changes in the DNA sequence (e.g., somatic point mutations) are the most frequent class of variants associated with the development of solid tumors and span common oncogenic events, such as NRAS, PIK3CA and BRAF mutations, in addition to KRAS mutations.

The classical approach used in microarray genotyping, based on spotting specific capture sequences at different locations of the microarray, fails in detecting minority point mutations. When a small amount of mutated sequence is present in a large amount of wild type background, high analytical sensitivity and specificity are required. In classical SNP microarray detection, after denaturation, only one PCR strand is captured on the surface. However, due to re-annealing with the complementary strand and steric hindrance of the surface, the capture efficiency is extremely low with dramatic consequences on assay sensitivity. Multiplexing the mutations detected is even more challenging as it is difficult to design capture reporters that bind selectively to their complementary PCR strand at a single temperature. Previous attempts to overcome this problem using the "amplicon down"[25] format were successful allowing high sensitive detection of single mutations. Unfortunately, some drawbacks hampered the application of the assay with real clinical samples. In the "amplicon down" approach, many different PCR products are spotted and subsequently denatured and hybridized with two oligonucleotides labeled with Cy3 and Cy5 complementary to both, the wild type and the mutated sequence. With this approach, it is possible to genotype, in a single chip, samples from several patients, but each mutation requires a distinct chip. In addition, PCR products obtained in clinical settings must be arrayed on silicon slides making the assay impractical and cumbersome.

In this study, a new sequence of operations was devised that render the assay highly multiplexable and robust. The biotinilated forward primer allowed to bind the PCR product with streptavidin modified magnetic beads. The amplicon, bound to magnetic beads, was subjected to thermal denaturation (5 minutes at 95° C.) and quickly placed on a magnet. The supernatant with the single strand DNA was recovered while the magnetic beads, with the biotinylated strand, were discharged. The single strand amplicon was hybridized in solution with oligonucleotide reporters. Removal of the unwanted DNA strand was important to increase the assay sensitivity as it prevents the reannealing of the two strands before hybridization with the reporters.

The sequence of steps that follows amplification is summarized in FIG. 2 for this embodiment.

The single strand PCR was incubated for 10 minutes with the stabilizer oligonucleotides to prevent formation of secondary structures in the DNA that would hamper the hybridization with the specific reporters. For some mutations, this step is an important part of the process, as in the absence of the stabilizer, the assay did not work in some cases (data not shown).

The specificity of the assay described here relies largely on the allele-specific in-tube hybridization (10 minutes) of the dual-domains reporters with the single strand amplicons encompassing the mutation sites at a specific hybridization temperature. The sequences of stabilizer and reporter oligonucleotides, designed to detect the most common mutation in KRAS, BRAF, PIK3CA and NRAS, are shown in Tables 1, 2, 3, and 4, respectively. By carrying out the hybridization in solution, the yield and specificity of the molecular recognition were greatly improved. The key point for the successful genotyping by microarray technique was to decouple sequence recognition from surface capture. Solution hybridization allowed to carry out the recognition in a thermal gradient so that each reporter oligonucleotide could bind to the amplicon in optimal conditions. Finally, the solution containing the single strand PCR, hybridized with the dual-domain reporters, contacts the microarray surface. Oligonucleotides (barcode probes), 20-21 bases, were covalently bound, at known locations, on the surface of silicon chips coated with three-dimensional copolymer, called copoly (DMA-NAS-MAPS). These barcode probes hybridize specifically to the dual-domain reporters containing sequences complementary to the barcode. The selection of the barcode probe sequences is important because it affects the efficiency and the specificity of the detection. To minimize cross-hybridization with dual-domain oligonucleotide reporters and with universal oligonucleotide labeled with Cy3 (U-Cy3) the barcode probes were tested experimentally for cross-hybridization (data not shown). Importantly, since the barcode probes are artificial sequences, a number of mutations can be detected using the same barcoded microarray simply by changing the portion of the dual domain reporter that is complementary to the mutated sequence.

Figure 3:
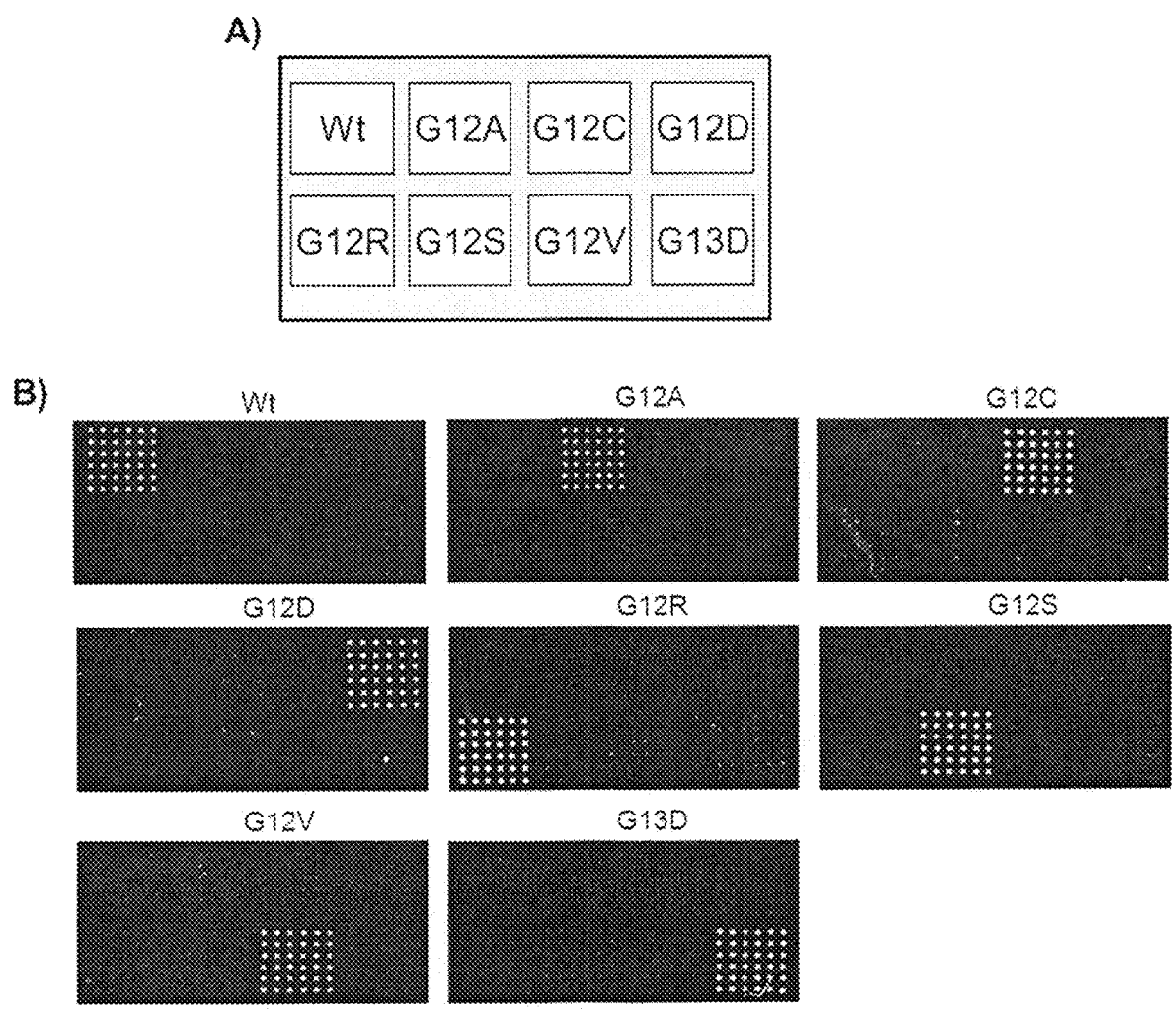

To evaluate the reliability of this KRAS mutation test, genomic DNA was examined which was extracted from subjects carrying different mutations in KRAS codon 12 (G12A, G12C, G12D, G12R, G12S, G12V) and 13 (G13D) and in wild-type control. As shown in FIG. 3 and FIG. 5, the test was successful in correctly genotyping all the seven KRAS mutations. An intense fluorescence signal appeared only at the location where oligonucleotides complementary to the barcode sequence are immobilized with, very low cross-hybridization and a good reproducibility from spot to spot.

1.3. Detection Limit

Clinical tumor samples, mainly coming from formalin-fixed paraffin embedded (FFPE) tissues, are typically composed of both wild-type and mutant DNA, with the proportion of wild-type DNA often vastly exceeding that of the mutant. This is true also for circulating tumor DNA, the typical marker in liquid biopsy. The PCR sequencing method, which is generally considered a gold standard for clinical diagnosis, is reliable only when the mutant-to-wild ratio reaches 10%-20%[31]. It is very difficult to obtain homogenous tumor samples in the clinical setting and so mutation content can be below the limit of detection of PCR sequencing. Thus, more sensitive KRAS mutation-testing methods are urgently needed to improve clinical diagnosis. The experiments evaluated the sensitivity of this system with serial dilution (5%; 2.5%; 1.25%; 0.62%; 0.31%; 0.075%; 0.037%) of mutated DNA opportunely mixed with wild-type DNA.

In particular, a heterozygous reference standard by Diatech Pharmacogenetics (50% mutated G12D allele) was used as starting point. The microarray system described here was able to detect a minimum of about 0.075% of mutated allele in a background of wild-type DNA for the G12D mutation (FIG. 4). This is a large, unexpected improvement over the sensitivity of PCR sequencing which could detect as few as 10% mutants. This level of sensitivity is mandatory in liquid biopsy to detect mutations in cell free circulating DNA.

1.4. Detection of KRAS mutations in Formalin-Fixed Paraffin-Embedded (FFPE) cancer tissues.

The assay was validated by analysing DNA extracted from FFPE clinical samples from subjects either mutated or wild-type for the KRAS gene, previously characterized by the QX100™ Droplet Digital™ PCR (ddPCR) System (Bio-Rad). The results obtained are shown in FIG. 5. The assay is able to detect unambiguously the correct mutation in each clinical samples analysed.

Moreover, to evaluate the applicability of the tag-microarray approach in a real clinical setting we performed a blind analysis of 15 FFPE samples. In order to correctly genotype the tumour DNA with a single chip, the single stranded PCR was hybridized with a mixture of the seven specific reporters in a stepwise gradient of temperature ranging from 41° C. (the hybridization temperature specific for the G12C mutation) to 29° C. (the hybridization temperature specific for the G12V mutation). The mixture was kept for 5 minutes at 41, 37, 36 and 30 and 29° C. corresponding to the hybridization temperatures of G12C, G12D, G13D, G12S, G12A, G12R and G12V mutations, respectively. All of the 15 samples were analyzed in parallel and correctly genotyped in less than 40 minutes. A typical result is shown in FIG. 6 for the sample identified with the G12S mutation. The wild type is always present while different 6×6 spot replicates at different locations on the slide highlight depending on the mutation detected.

2. Experimental Section 2.1. Samples 15 formalin-fixed paraffin-embedded (FFPE) samples were analyzed with this procedure.

Circulating tumor DNA was extracted with the automatic extractor Maxwell® RSC (Promega) using the Maxwell® RSC ccfDNA Plasma Kit (cat. AS1480).

To assess the sensitivity of the method a dilution curve was generated starting from a heterozygous reference standard by Diatech Pharmacogenetics (50% mutated allele) mixed with wild-type DNA in a proportion mimicking the concentration of tumor DNA in plasma of cancer patients.

2.2. PCR Conditions

Exon 2 of the KRAS gene was amplified with the following primer set: biotin-5'-GCC TGC TGA AAA TGA CTG AA-3' (SEQ ID NO: 1) (biotin-forward) and 5'-CTG AGT CCG AAC ATT GAG AGA ATG GTC CTG CAC CAG TAA-3' (SEQ ID NO: 2) (5'-tag-reverse) generating a 167 bp fragment.

PCR was performed in 25 µL reaction containing 15 ng of DNA, 200 µM of each deoxynucleotide, 10 mM Tris-HCl (pH 8.3), 50m M KCl, 1.5 mM $MgCl_2$, 1 U of DNA polymerase (FastStart; Roche,) and 10 pmoles of each primer. Cycling conditions entailed an initial denaturation at 95° C. for 10 min followed by 35 cycles at 95° C. for 30 s, 58° C. for 30 s and 72° C. for 30 s, and a final elongation at 72° C. for 10 min.

2.3. Silicon Slide Coating and Microarray Preparation

Untreated silicon 1000 Å Thermal Oxide (14×14 mm) chips were supplied by SVM, Silicon Valley Microelectronics Inc. (Santa Clara, Calif. USA). After an activation treatment (15 min) with oxygen plasma, the silicon chips were immersed for 30 min in a solution (1% w/v in 0.9 M $(NH4)_2SO_4$ water solution) of a modified form of copoly (DMA-NAS-MAPS) with 10% NAS moiety. The copoly (DMA-NAS-MAPS) was synthesized and characterized as described[26] but to enhance the binding capacity of the copolymer (terpolymer), the N-acryloyloxysucinimide (NAS) molar fraction was increased from 2% to 10%. The slides were finally rinsed with water and dried under vacuum at 80° C. for 20 minutes. Eight different oligonucleotides sequences were selected between those reported in Battistella et al.[32] as capture probes to be spotted on silicon chips corresponding to the seven KRAS mutations and to the wild-type sequence (Table 1). These oligonucleotides were originally selected from the GeneFlex™ Tag Array collection (Affymetrix, Santa Clara, Calif.) that contains sequence information for 2000 oligonucleotides with minimal tendency for cross-hybridization. The capture probes, amino modified at the 5' end, from Metabion International AG (Steinkirchen, Germany), were dissolved in the printing buffer (150 mM sodium phosphate pH 8.5, 0.01% Sucrose monolaurate) at a concentration of 10 µM and printed in 36 replicates (6×6 sub-arrays) using a piezoelectric spotter, SciFLEX ARRAYER S5 (Scienion, Berlin, Germany). Spotting was performed at 20° C. in an atmosphere of 60% humidity. After the spotting step the chips were placed in an uncovered storage box, laid in a sealed chamber, saturated with sodium chloride (40 g/100 mL H$_2$O), and incubated overnight. After incubation, all residual reactive groups of the coating polymer were blocked by dipping the chips in a pre-warmed blocking solution (50 mM ethanolamine, 0.1 M Tris, pH 9.0) at 50° C. for 15 minutes, followed by rinsing twice in distilled H$_2$O. Chips were washed in pre-warmed, post-coupling washing solution, 4× saline sodium citrate (SSC), 0.1% (w/v) sodium dodecyl sulfate (SDS), at 50° C. for 15 minutes, rinsed with distilled H$_2$O, dried by nitrogen flux.

2.4. Preparation of Single-Strand DNA from PCR Products with Streptavidin Magnetic Beads and Liquid Allele-Specific Hybridization Prior to use, the streptavidin-coated magnetic beads (Dynabeads™ M-270 Streptavidin, Invitrogen) were washed three times with Binding and Washing buffer (B&W) (5 mM Tris-HCl, pH 7.5; 0.5 mM EDTA; 1M NaCl) according to the manufacturer's protocol. Afterwards the streptavidin-coated beads (250 µg) were added to a PCR tube containing 25 µL of biotinylated PCR product and 75 µL of B&W buffer and incubated at room temperature for 10 minutes with gentle rotation. The beads with the bound PCR products were then washed 2-3 times in the B&W buffer and resuspend in 30 µL of the same buffer and heated to 95° C. for 5 minutes. At the end of the denaturation step, the PCR tube was placed on a magnet and the supernatant with the single-strand PCR (29.1 µL) was transferred to a fresh tube containing 0.9 µL of a 10 µM stabilizer, an oligonucleotide necessary to open the secondary structures present in the amplicon, (final concentration 0.3 µM) and incubated with this oligonucleotide for 10 minutes at room temperature, while the beads with the bound biotinilated PCR strand were discharged. Then for the detection of wild-type and G12A, G12C, G12D, G12R, G12S, G12V, and G13D KRAS mutations, the reporter for the wild-type and the mutated sequences were added together in equimolar amounts (final concentration 0.1 µM) to the tube containing the ssPCR-stabilizer solution (final volume 40 µL). The incubation lasted for 35 minutes with gentle rotation in a stepwise gradient of temperature with steps corresponding to the hybridization temperatures specific for the seven mutations (see Table 1).

2.5. Microarray Hybridization, Image Scanning and Data Analysis

After the liquid allele-specific hybridization, to detect the KRAS mutations, the universal oligonucleotides labelled with Cy3 (Universal-Cy3) was added to the ssPCR-reporters solution to a concentration of 0.3 µM. The solution was then spread onto the spotted silicon chips and cover slips were placed on the spotted area. The chips were incubated at room temperature for 15 min in a humid hybridization chamber.

Finally the silicon chips were removed from the hybridization chamber and soaked briefly in 4×SSC buffer to remove the cover slips, washed twice for 5 min in 2×SSC/ 0.1% SDS, at room temperature, then dipped, in sequence, in a solution 0.2×SSC and 0.1×SSC for 1 min at room temperature, dried with a nitrogen flow and scanned. ProScanArray (Perkin Elmer, MA, USA) was used to scan the hybridized chips. In particular a green laser ($\lambda_{ex}$ 543 nm/$\lambda_{em}$ 570 nm) for the Cy3 dye was applied. The photomultiplier (PMT) tube gain and the laser power changed between different experiments. 16-bit TIFF images were analysed at 5 µm resolution. Data intensities were extracted with the scanner (Scanarray Express) and the data analysis was performed for each experiment.

Unexpected Conclusions

In summary, in this preferred embodiment, a microarray platform is described for rapid, specific and sensitive detection of mutations in codon 12 and 13 of the KRAS gene suitable for high-throughput analysis without costly instrumentation.

It was highly unexpected that a microarray based analysis reached the level of sensitivity reported by this work in the detection of minority mutations. The most significant advantage of this system is the ability to separate the mutation detection from the array hybridization without the use of enzymatic reactions such as ligases or single base extensions. Each step was improved separately, and therefore the sensitivity and accuracy of this method were significantly enhanced. Direct hybridization DNA microarrays suffer from differential hybridization efficiencies owing either to sequence variation or to the amount of target present in the sample with an increase of background noise and false signals due to mismatch hybridization and non-specific binding. In contrast, this approach can readily distinguish all point mutations in solution and then the use of divergent surface barcode probe sequences with similar properties allows rapid hybridizations of the array at room temperature. Using the tag-microarray method, the genotyping of clinical sample, can be obtained in less than 90 minutes, thus, this assay greatly shortens the time of the operations compared, for example, to the method of direct sequencing which normally takes 1-2 working days.

Finally, the method proposed can be a universal approach since the spotted barcode probe sequences remain constant and their complements can be appended to any set of reporters that recognize multiple mutations in different codons or different genes. Thus a single array design can be programmed to detect a wide range of genetic mutations. This method is an innovative technique for routine diagnosis not only for KRAS mutations but also for a wide range of genetic variations (including BRAF, PIK3CA, and NRAS mutations, for example).

NEW WORKING EXAMPLES

To validate further the proposed mutation assay, an examination was carried out for the genomic DNA extracted from subjects carrying different mutations in KRAS codon 12 (G12A, G12C, G12D, G12R, G12S, G12V), 13 (G13D), 61 (Q61HC, Q61HT, Q61K, Q61L, Q61R) and 146 (A146T), in NRAS codon 12 (G12A, G12C, G12D, G12S, G12V) and 13 (G13D, G13R, G13V) and in BRAF codon 15 (V600E) and in wild-type controls. FIG. 12 shows the spotting scheme of the array and some examples of genotyping of KRAS (G12S, Q61R, A146T), NRAS (G13R) and BRAF (V600E) mutations. Correct genotyping of all the KRAS, NRAS and BRAF mutations considered was found. An intense fluorescence signal appears only at the location where oligonucleotides complementary to the barcode sequence were immobilized with very low cross-hybridization and a good signal reproducibility from spot to spot.

FIG. 12 shows (A) Schematic representation of the spotted barcode probe array. Silicon chips coated with copoly (DMA-NAS-MAPS) with 10% NAS was used as substrates for the covalent attachment of amino-modified barcode probe oligonucleotides spotted at discrete locations. Each position in the grid identifies an individual barcode probe address corresponding to KRAS codon 12-13 (yellow squares), KRAS codon 61 (orange squares), KRAS codon 146 (blue square), NRAS codon 12-13 (green squares) and BRAF mutations (red square). The light grey portion of the array is spotted with an amino-modified oligonucleotide (COCU8), not correlated with the genes, to be used as reference spots.

(B) Microarray scanning of the Cy3 fluorescence signal of five different silicon chips. Each robotically spotted array was hybridized with an individual single strand PCR incubated with dual-domain reporters that directs the construct to the correct address. The fluorescence detection is obtained incubating the array with a mixture of the universal Cy3 labeled oligonucleotide complementary to the tagged-reverse primer of the single strand PCR and with a Cy3-labeled oligonucleotide (COCU10) complementary to COCU8. KRASG12S, KRASQ61R, KRASA146T, NRASG13R and BRAF V600E correspond to the control sample containing the indicated mutation. All the five samples of known genotype (mutant homozygous or heterozygous in case of BRAF V600E) were correctly identified.

Lowest limit of detection LOD:

Clinical tumor samples, mainly coming from formalin-fixed paraffin embedded (FFPE) tissues, are typically composed of both wild-type and mutant DNA, with the proportion of wild-type DNA often vastly exceeding that of the mutant. It might be difficult to obtain homogenous tumor samples in clinical samples so mutated DNA content can be below the limit of detection of PCR sequencing. Even more challenging is the analysis of circulating tumor DNA (ctDNA) because of its low mutant allele frequency and large dynamic range. The level of ctDNA in cancer patients ranges from <0.1% to >50% out of the total cfDNA. Therefore, the technical sensitivity and dynamic range of the assay are important to introduce a ctDNA assay in clinics.

The sensitivity of the system was evaluated with serial dilution (2.5%; 1.25%; 0.62%; 0.31%; 0.15%; 0.075%) of mutated DNA opportunely mixed with wild-type DNA, with a total DNA amount of 20 ng. A calibration curve was built for each of the seven most common mutations of the KRAS gene, in order to calculate the lowest limit of detection (LOD) intended as the minimum mutational abundance that can be confidently detected by the assay. The probe array of FIG. 12, was spotted in 7 wells on a coated silicon slide. Using a 16-well incubation chamber (Nexterion® IC-16, SCHOTT), mixtures of wild type and mutated DNA in different ratios from 0 to 2.5% were incubated in parallel on different wells of the same slide (FIG. 13A). The control sample (0% mutant DNA) showed only a low fluorescence background signal. By plotting signal fluorescence versus percentage of mutated DNA it was possible to draw calibration curves, one for each mutation from which the LOD values were extrapolated. The FIG. 13C shows an example of calibration curve for the KRAS G12S mutation. The table (FIG. 13D) reports the limit of detection for each mutation. The determination of LOD is based on the equation: $3{,}3\sigma/s$ where s is the slope of calibration curve and $\sigma$ is standard deviation of fluorescence background of the spots of the wild type sample. The microarray system proposed here has a sensitivity that ranges from 0.03% for KRAS G12C and G12D mutations to 0.28% for KRAS G13D mutation.

FIG. 13(A) picture shows the setup utilized to realize the calibration curves for the KRAS codon 12-13 mutations. (B) Microarray scanning of the Cy3 signal of the coated silicon slide and the magnification of a portion of it showing the result of the hybridization of four different concentration of mutant DNA in four different wells. (C) Plot representing the relative fluorescence intensity of the signal corresponding to the Cy3-labeled mutated single strand PCR bound to the G12S barcode probe. The points, calculated as the average of the intensity of four spots, correspond to the percentage of the KRAS G12S mutation in a background of KRAS wild-type DNA. The value at point 0 represents the relative fluorescence intensity of the background presents on the G12S barcode probe array of the well hybridized with wild-type control sample. The error bars are the standard deviations of the fluorescence intensity of each well. The equation of the trend line of the graph is utilized to extrapolate the limit of detection (LOD) for the assay. (D) Table showing the extrapolated limits of detection for the seven most common mutations of the KRAS gene.

Detection of KRAS Mutations in Formalin-Fixed Paraffin-Embedded (FFPE) Cancer Tissues and in Cell-Free Circulating Tumor DNA (ctDNA):

To evaluate the applicability of the tag-microarray approach in a real clinical setting, an analysis was performed of 18 FFPE samples. The gene and the codon of the mutation were known but not the mutation itself. In order to correctly genotype the tumour DNA with a single chip, the single stranded PCR was hybridized with the mixture of all the specific reporters (22 mutant reporters and 5 wt reporters) in a stepwise gradient of temperature ranging from 42° C. to 29° C. All 18 samples were analyzed in parallel and correctly genotyped in less than 90 minutes. Typical results are shown in FIG. 14 for the samples identified with KRAS G12S (A), KRAS Q61HC (B) mutations and NRAS G12V (C) mutation. The corresponding wild type is always present while different 2×2 spot replicates at different locations on the slide highlight depending on the mutation detected.

FIG. 14 shows that the spotting schema of the barcode sequences is the same of FIG. 12A. (A) Cy3 fluorescence image and the plot of the relative fluorescence intensity of the sample identified with KRAS G12S mutation. (B) Cy3 fluorescence image and the plot of the relative fluorescence intensity of the sample identified with KRAS Q61HC mutation. (C) Cy3 fluorescence image and the plot of the relative fluorescence intensity of the sample identified with NRAS G12V mutation. The bars are the average of the intensity of the 4 spots (2×2 subarray) of each barcode probe subarrays. The error bars are the standard deviations of the fluorescence intensity of each sample.

To evaluate the applicability of the tag-microarray approach in a real clinical setting, an analysis was performed of 3 liquid biopsy samples using circulating tumour DNA (ctDNA). FIG. 15 shows a typical fluorescence image of the array used to detect one of the 22 mutations reported in the scheme of FIG. 12. ctDNA of three patients, two mutated and one wild type are analyzed. While the wild type signals is always present (top left), only mutated DNA generate the signals in the squares. From the intensity of these signals the concentration of mutated DNA can be assessed through a calibration curve.

CORE/DENDRIMER EMBODIMENT AND WORKING EXAMPLES

Also provided, as describe above, is a composition comprising at least one reporter molecule which comprises at least two, different domains of oligonucleotide, wherein a first domain of oligonucleotide is for hybridization with the single strand amplification product, and wherein the second domain of oligonucleotide is for hybridization to at least one microarray probe surface, and which further comprises a core which is surface functionalized with the first domain and the second domain.

In particular, an additional preferred embodiment related to polymers, dendrimers, and/or dendrons is provided. See, for example, FIGS. 7-11. Dendrimers and dendrons are known in the art. See, for example, Dendrimers and Other Dendritic Polymers, J. M. J. Frechet and D. A. Tomalia, Eds. 2001; see also, U.S. Pat. Nos. 7,138,121; 5,175,270; and 6,806,047. As used herein, the dendrimer can be a highly branched structure. Dendrimers can be a molecule which comprises at inner, branched core structure which has a surface around the core, and this surface can be reactive and can be functionalized. Functionally useful groups including oligonucleotides can be attached covalently to the surface. Multiple types of groups can be attached, and the ratio of the amounts of the different groups can be controlled to provide for a useful or optimal outcome. Different types of dendrimers can be made, but a preferred example is an azido dendrimer. See, for example, PCT/US15/65319. An example is an azido dendrimer, bis-MPA-Azide dendrimer with trimethylol propane core, generation three. Click chemistry can be used to functionalize the dendrimer. In one embodiment, the dendrimer, which is further functionalized at the surface, is a synthetic polymer and not a dendritic polynucleotide (as in 5,175,270).

In this embodiment, the reporter molecule of the hybridization step can further comprise at least one dendrimer which is covalently bound to the first domain and the second domain. Hence, the first domain of oligonucleotide, which is for hybridization with the single strand amplification product, can be attached to the dendrimer surface, and the second domain of oligonucleotide, which is for hybridization to at least one microarray probe surface, also can be attached to the same dendrimer surface.

The ratio of the first domain to the second domain can be, for example, 20:1 to 1:20, or 10:1 to 1:10, 10:1 to 1:1, or 5:1 to 3:1, or about 4:1.

Another aspect provides for an assay method for a gene fragment of interest comprising:

amplify at least one gene fragment of interest comprising or potentially comprising at least one SNP region of interest to form an initial amplification product, wherein the fragment to be amplified is primed in the amplification to enable (1) isolation of one single strand from another single strand of the initial amplification product in a later step of the assay, and (2) detection of the isolated single strand in a later step in the assay;

isolate at least one single strand amplification product from the initial amplification product, wherein the single strand amplification product either comprises or potentially comprises the at least one SNP region of interest;

hybridize in solution the single strand amplification product with at least one reporter molecule which comprises at least two, different domains of oligonucleotide, wherein a first domain of oligonucleotide is for hybridization with the single strand amplification product, and wherein the second domain of oligonucleotide is for hybridization to at least one microarray probe surface, wherein the microarray probe surface comprises at least one capture probe to allow for hybridization;

contact the solution of the hybridized single strand amplification product with the at least one microarray probe surface which comprises at least one capture probe to allow for hybridization;

detect for the presence of the hybridized single strand amplification product on the microarray surface, wherein the reporter molecule comprises a core which is surface functionalized with the first domain and the second domain.

Another aspect provides for an assay method for a gene fragment of interest comprising:

amplify at least one gene fragment of interest comprising or potentially comprising at least one SNP region of interest to form an initial amplification product, wherein the fragment to be amplified is primed in the amplification to enable (1) isolation of one single strand from another single strand of the initial amplification product in a later step of the assay, and (2) detection of the isolated single strand in a later step in the assay;

isolate at least one single strand amplification product from the initial amplification product, wherein the single strand amplification product either comprises or potentially comprises the at least one SNP region of interest;

hybridize in solution the single strand amplification product with at least one reporter molecule which comprises at least two, different domains of oligonucleotide, wherein a first domain of oligonucleotide is for hybridization with the single strand amplification product, and wherein the second domain of oligonucleotide is for hybridization to at least one microarray probe surface, wherein the microarray probe surface comprises at least one capture probe to allow for hybridization;

contact the solution of the hybridized single strand amplification product with the at least one microarray probe surface which comprises at least one capture probe to allow for hybridization;

detect for the presence of the hybridized single strand amplification product on the microarray surface, wherein the reporter molecule is a composition as described and/or claimed herein.

In some embodiments, the core is a polymeric core. In some embodiments, the core is free on nucleotides. In some embodiments, the core is a water-soluble polymer core. In some embodiments, the core is a dendrimer core. In some embodiments, the core is a dendron core. In some embodiments, the core is covalently bound to the first domain and the second domain. In some embodiments, the core is an azido dendrimer core which is covalently bound to the first domain and the second domain.

In some embodiments, the core is a dendrimer core which is covalently bound to the first domain and the second domain, and the ratio of the first domain to the second domain is about 10:1 to 1:1.

In some embodiments, the composition is adapted for use in a microarray assay for genotyping of a gene fragment of interest, as described above including the Working Examples above. In some embodiments, the composition is adapted for use in detection of a single mutation of an oncogene. In some embodiments, the composition is adapted for use in the detection of at least one single mutation in a KRAS, NRAS, BRAF, and/or PIK3CA oncogene. In some embodiments, the first domain is for the detection of at least one single mutation in a KRAS oncogene. In some embodiments, the first domain is for the detection of at least one KRAS oncogene mutation at codon 12, and/or codon 13, and/or codon 61, and/or codon 146. In some embodiments, the first domain is for the detection of at least one KRAS oncogene mutation at codon 12 and/or codon 13. In some embodiments, the first domain is for the detection of at least one KRAS oncogene mutation which includes at least one of G12A, G12C, G12D, G12R, G12S, and/or G12V in codon 12; and/or G13D in codon 13; and/or Q61HC Q61HT, Q61L, Q61R, and/or Q61K in codon 61; and/or A146T in codon 146 mutations. In some embodiments, the first domain is for detection of at least one single mutation in an NRAS oncogene. In some embodiments, the first domain is for detection of at least one NRAS oncogene mutation at codon 12 and/or 13. In some embodiments, the first domain is for detection of at least one NRAS oncogene mutation which includes at least one of G12A, G12C, G12D, G12S, G12V in codon 12, and/or G13D, G13R, G13V in codon 13 mutations. In some embodiments, the first domain is for the detection of at least one single mutation in a BRAF oncogene. In some embodiments, the first domain is for the detection of at least one BRAF mutation at codon 600. In some embodiments, the first domain is for the detection of one BRAF oncogene mutation which is the V600 E in codon 600 mutation. In some embodiments, the first domain is for the detection of at least one single mutation in a PIK3CA oncogene. In some embodiments, the first domain is for the detection of at least one PIK3CA mutation at codon 542, 545, and/or 1047. In some embodiments, the first domain is for the detection of at least one PIK3CA mutation which includes at least one of E542K in codon 542 mutation, E545K in codon 545 mutation, and H1047R in codon 1047 mutation. In some embodiments, the ratio of the first domain to the second domain is about 10:1 to 1:10. In some embodiments, the ratio of the first domain to the second domain is about 10:1 to 1:1. In some embodiments, the composition comprises at least two of the reporter molecules, which are different, and at least one solvent for the two different reporter molecules.

Other embodiments provide for an assay comprising the step of hybridization using the reporter molecule as described and/or claimed herein.

Other embodiments provide for a method of making the reporter molecule as described and/or claimed herein comprising surface functionalizing the core with the first domain and the second domain.

Other embodiments provide for a kit comprising the reporter molecule as described and/or claimed herein.

ADDITIONAL WORKING EXAMPLES

Additional non-limiting working examples are described below.

Materials 2,2-bis(hydroxymethyl)propionic acid-Azide dendrimer trimethylol propane core, generation 3 was purchased from Sigma-Aldrich. The dendrimer has 24 azide surface groups.

Oligonucleotide Wt and Mut were purchased from Metabion International AG (Steinkirchen, Germany) and have the following sequences:

```
Spotting probe Wt:
                                        (SEQ ID NO: 3)
NH2 5'-actccagtgccaagtacgat-3'

Spotting probe Mut:
                                        (SEQ ID NO: 4)
NH2 5'-ggctcacgtcttatttgggc-3'

Oligo 1 complementary to probe Wt:
                                        (SEQ ID NO: 5)
DBCO 5'atcgtacttggcactggagt-3'

Oligo 3 complementary to PCR Wt:
                                        (SEQ ID NO: 6)
5'-CTGGTGGCGTA-3' DBCO Oligo 2 complementary to probe Mut:
                                        (SEQ ID NO: 7)
DBCO 5'gcccaaataagacgtgagcc-3'

Oligo 4 complementary to PCR Mut:
                                        (SEQ ID NO: 8)
5'-GCTGATGGCGT-3' DBCO Universal-Cy3 (complementary to the reverse tag
primer of PCR):
                                        (SEQ ID NO: 9)
5'-ctcaatgttcggactcag-3'
```

Methods

Preparation of Single-Strand DNA from PCR Products with Streptavidin Magnetic Beads and Liquid Allele-Specific Hybridization Prior to use, the streptavidin-coated magnetic beads (Dynabeads™ M-270 Streptavidin, Invitrogen) were washed three times with Binding and Washing buffer (B&W) (5 mM Tris-HCl, pH 7.5; 0.5 mM EDTA; 1M NaCl) according to the manufacturer's protocol. Afterwards the streptavidin-coated beads (250 μg) were added to a PCR tube containing 25 μL of biotinylated PCR product and 75 μL of B&W buffer and incubated at room temperature for 10 minutes with gentle rotation. The beads with the bound PCR products were then washed 2-3 times in the B&W buffer and resuspended in 30 μL of the same buffer and heated to 95° C. for 5 minutes. At the end of the denaturation step, the PCR tube was placed on a magnet and the supernatant with the single-strand PCR (29.1 μL) was transferred to a fresh tube containing 0.9 μL of a 10 μM stabilizer (sequence: 5'-gcaagagtgccttgacgatacagctattcag-3') (SEQ ID NO: 28), an oligonucleotide necessary to open the secondary structures present in the amplicon, (final concentration 0.3 μM) and incubated with this oligonucleotide for 10 minutes at room temperature, while the beads with the bound biotinylated PCR strand were discharged.

Conjugation of Oligonucleotides to Azido Dendrimer

Oligonucleotides were bound to the dendrimer in a 4:1 ratio: the oligonucleotide complementary to the PCR is 4 fold the oligonucleotide complementary to the spotted probe. The azide dendrimer stock solution in DMSO is diluted to 42 uM in TBS buffer (0.5 mM Tris-HCl pH 7.5 0.05 mM EDTA 0.1 M NaCl); then 0.5 μL of this solution are added to a 4:1 mixture of Oligo 3 and Oligo 1, both 100 uM in water (4 μL and 1 μL respectively) and incubated overnight at 37° C. (Wt dendrimer). Similarly Oligo 4 and 2 were conjugated to the azido dendrimer (Mut dendrimer) (FIG. 8).

The two solutions of Wild type dendrimer and mutant dendrimer were then mixed to obtain a single solution containing both the Wt and Mut dendrimer; then 0.4 μL of this solution were added to 40 μL of wild type or mutant single strand PCR (prepared as previously described) together with 0.3 μM of Universal-Cy3 for fluorescence detection. The solutions were incubated at room temperature for 1 h (FIG. 9).

Silicon Slide Coating and Microarray Preparation

Untreated silicon 1000 Å Thermal Oxide (14×14 mm) chips were supplied by SVM, Silicon Valley Microelectronics Inc. (Santa Clara, Calif. USA). After an activation treatment (15 min) with oxygen plasma, the silicon chips were immersed for 30 min in a copoly (DMA-NAS-MAPS) solution (1% w/v in 0.9 M (NH4)$_2$SO$_4$ water solution). The copoly (DMA-NAS-MAPS) was synthesized and characterized as described elsewhere[26]. The slides were finally rinsed with water and dried under vacuum at 80° C. for 20 minutes.

The capture probes (spotting probe Wt and spotting probe Mut), amino modified at the 5' end, from Metabion International AG (Steinkirchen, Germany), were dissolved in the printing buffer (150 mM sodium phosphate pH 8.5, 0.01% Sucrose monolaurate) at a concentration of 10 μM and printed in 64 replicates (8×8 sub-arrays) using a piezoelectric spotter, SciFLEX ARRAYER S5 (Scienion, Berlin, Germany). Spotting was performed at 20° C. in an atmosphere of 60% humidity. After the spotting step the chips were placed in an uncovered storage box, laid in a sealed chamber, saturated with sodium chloride (40 g/100 mL H$_2$O), and incubated overnight. After incubation, all residual reactive groups of the coating polymer were blocked by dipping the chips in a pre-warmed blocking solution (50 mM ethanolamine, 0.1 M Tris, pH 9.0) at 50° C. for 15 minutes, followed by rinsing twice in distilled H$_2$O. Chips were washed in pre-warmed, post-coupling washing solution, 4× saline sodium citrate (SSC), 0.1% (w/v) sodium dodecyl sulfate (SDS), at 50° C. for 15 minutes, rinsed with distilled H$_2$O, dried by nitrogen stream.

Each chip was then incubated in a humid chamber for 1 h at room temperature with 15 uL of the solution of dendrimers hybridized with the Wt or Mut PCR. In particular, Chip A was incubated with the Wt PCR modified dendrimer, while Chip B was incubated with the Mut PCR modified dendrimer.

After the incubation the chips were removed from the hybridization chamber and soaked briefly in 4×SSC buffer to remove the cover slips, washed twice for 5 min in 2×SSC/0.1% SDS, at room temperature, then dipped, in sequence, in a solution 0.2×SSC and 0.1×SSC for 1 min at room temperature, dried with a nitrogen flow and scanned. ProScanArray (Perkin Elmer, MA, USA) was used to scan the hybridized chips. In particular a green laser ($\lambda_{ex}$ 543 nm/$\lambda_{em}$ 570 nm) for the Cy3 dye was applied. The photomultiplier (PMT) tube gain was set at 80 and the laser power at 90. 16—Data intensities were extracted with the scanner (Scanarray Express) and the data analysis was performed for each experiment.

Results

In this preferred embodiment, each dendrimer was modified with two oligonucleotide: one is complementary to the probe immobilized onto the silicon chip, while the other is complementary to a sequence of the PCR, as shown in FIG. 10.

In this preferred embodiment, the optimal ratio between the two oligonucleotide is 4:1, and in particular the oligonucleotide complementary to the PCR is 4 fold the oligonucleotide complementary to the spotted probe.

As shown in FIG. 11A, each chip is spotted with both the Wt and the mutant probe; consequently each chip is hybridized with a solution containing both the Wt dendrimer and the Mut dendrimer. The fluorescence images (FIG. 11B) indicate that the Wt DNA is captured to the surface through the barcode sequence highly specifically. Mut PCR is captured by its dendrimer in solution and captured on the surface by its barcode sequence. The specificity in this case is not 100% as a small amount of dendrimer functionalized with oligonucleotides complementary to the mutated sequence are captured by the wild type barcode sequence. Since the main goal is to assess the presence of mutant DNA, this type of cross-talk does not compromise the quality of the assay. The intensity of fluorescence signals relative to wild type and mutated captured dendrimers is reported in FIG. 11.

REFERENCES

1. Pajic, M., et al. Preclinical strategies to define predictive biomarkers for therapeutically relevant cancer subtypes. *Hum. Genet.* 130, 93-101 (2011).
2. Sham, P. C. et al. Whole-genome association studies of complex diseases. *Curr. Orthop.* 22, 251-258 (2008).
3. Herreros-Villanueva, M., et al. KRAS mutations: analytical considerations. *Clin. Chim. Acta.* 431, 211-20 (2014).
4. Huggett, J. F. & Whale, A. Digital PCR as a novel technology and its potential implications for molecular diagnostics. *Clin. Chem.* 59, 1691-3 (2013).
5. Gentalen, E. & Chee, M. A novel method for determining linkage between DNA sequences: hybridization to paired probe arrays. *Nucleic Acids Res.* 27, 1485-91 (1999).
6. Huang, J. X. et al. High-Throughput Genomic and Proteomic Analysis Using Microarray Technology. *Clin. Chem.* 47, (2001).
7. LaFramboise, T. Single nucleotide polymorphism arrays: a decade of biological, computational and technological advances. *Nucleic Acids Res.* 37, 4181-4193 (2009).
8. Hoffman, M. Getting a handle on Ras activity. *Science* (80-.). 255, (1992).
9. Kiaris, H. & Spandidos, D. MUTATIONS OF RAS GENES IN HUMAN TUMORS (REVIEW). *Int. J. Oncol.* (1995). doi:10.3892/ijo.7.3.413
10. Shirasawa, S., et al., Altered growth of human colon cancer cell lines disrupted at activated Ki-ras. *Science* (80-.). 260, (1993).
11. Yanez, L., Groffen, J. & Valenzuela, D. M. c-K-ras mutations in human carcinomas occur preferentially in codon 12. *Oncogene* 1, 315-8 (1987).
12. Karapetis C S, Maru D, Waring P, Tie J, Michael M Z. Incorporating traditional and emerging biomarkers in the clinical management of metastatic colorectal cancer, *Expert Review of Molecular Diagnostics,* 2015; 15:1033-48.
13. Wang, J. et al. Direct sequencing is a reliable assay with good clinical applicability for KRAS mutation testing in colorectal cancer. *Cancer Biomark.* 13, 89-97 (2013).
14. Lin, M.-T. et al. Clinical Validation of KRAS, BRAF, and EGFR Mutation Detection Using Next-Generation Sequencing. *Am. J. Clin. Pathol.* 141, (2014).
15. Toyooka, S. et al. Detection of codon 61 point mutations of the K-ras gene in lung and colorectal cancers by enriched PCR. *Oncol. Rep.* 10, 1455-9 (2003).
16. Luo, J.-D. et al. Detection of rare mutant K-ras DNA in a single-tube reaction using peptide nucleic acid as both PCR clamp and sensor probe. *Nucleic Acids Res.* 34, e12 (2006).
17. Mixich, F., Ioana, M., Voinea, F., Săftoiu, A. & Ciurea, T. Noninvasive detection through REMS-PCR technique of K-ras mutations in stool DNA of patients with colorectal cancer. *J. Gastrointestin. Liver Dis.* 16, 5-10 (2007).
18. Dieterle, C. P., Conzelmann, M., Linnemann, U. & Berger, M. R. Detection of Isolated Tumor Cells by Polymerase Chain Reaction-Restriction Fragment Length Polymorphism for K-ras Mutations in Tissue Samples of 199 Colorectal Cancer Patients. *Clin. Cancer Res.* 10, (2004).
19. Lopez-Crapez, E., Chypre, C., Saavedra, J., Marchand, J. & Grenier, J. Rapid and large-scale method to detect K-ras gene mutations in tumor samples. *Clin. Chem.* 43, 936-42 (1997).
20. Parsons, B. L. et al. ACB-PCR Quantification of K-RAS Codon 12 GAT and GTT Mutant Fraction in Colon Tumor and Non-Tumor Tissue. *Cancer Invest.* 28, 364-375 (2010).
21. Maekawa, M. et al. Three-Dimensional Microarray Compared with PCR-Single-Strand Conformation Polymorphism Analysis/DNA Sequencing for Mutation Analysis of K-ras Codons 12 and 13. *Clin. Chem.* 50, (2004).
22. Liu, Y., Gudnason, H., Li, Y., Bang, D. D. & Wolff, A. An oligonucleotide-tagged microarray for routine diagnostics of colon cancer by genotyping KRAS mutations. 1556-1564 (2014). doi:10.3892/ijo.2014.2541
23. Favis, R., Gerry, N. P., Cheng, Y.-W. & Barany, F. Applications of the universal DNA microarray in molecular medicine. *Methods Mol. Med.* 114, 25-58 (2005).
24. Gerry, N. P. et al. Universal DNA microarray method for multiplex detection of low abundance point mutations. *J. Mol. Biol.* 292, 251-62 (1999).
25. Galbiati, S. et al. A new microarray substrate for ultrasensitive genotyping of KRAS and BRAF gene variants in colorectal cancer. *PLoS One* 8, e59939 (2013).
26. Pirri, G., Damin, F., Chiari, M., Bontempi, E. & Depero, L. E. Characterization of a polymeric adsorbed coating for DNA microarray glass slides. *Anal. Chem.* 76, 1352-8 (2004).
27. Cretich, M. et al. High sensitivity protein assays on microarray silicon slides. *Anal. Chem.* 81, 5197-203 (2009).
28. Damin, F., Galbiati, S., Ferrari, M. & Chiari, M. DNA microarray-based solid-phase PCR on copoly (DMA-NAS-MAPS) silicon coated slides: An example of relevant clinical application. *Biosens. Bioelectron.* 78, 367-373 (2016).
29. Jacobson, D. R. & Mills, N. E. A highly sensitive assay for mutant ras genes and its application to the study of presentation and relapse genotypes in acute leukemia. *Oncogene* 9, 553-63 (1994).
30. Allegra, C. J. et al. American Society of Clinical Oncology provisional clinical opinion: testing for KRAS gene mutations in patients with metastatic colorectal carcinoma to predict response to anti-epidermal growth factor receptor monoclonal antibody therapy. *J. Clin. Oncol.* 27, 2091-6 (2009).
31. Tsiatis, A. C. et al. Comparison of Sanger Sequencing, Pyrosequencing, and Melting Curve Analysis for the Detection of KRAS Mutations Diagnostic and Clinical Implications. (2010). doi:10.2353/jmoldx.2010.090188.
32. Battistella, S. et al. Genotyping δ-Globin Gene Mutations on Copolymer-Coated Glass Slides with the Ligation Detection Reaction. *Clin. Chem.* 54, (2008).

Additional Description

A rapid and sensitive microarray-based assay is described for the detection of single mutations in, for example, the KRAS oncogene. In one third of human cancers, KRAS mutations are present which play a critical role in early development of cancer and resistance to standard therapeutic regimen. KRAS point mutations cluster in several hotspots principally involving codons 12 and 13. Therefore, in clinical practice it is important to identify the correct KRAS mutational status. In a preferred embodiment of the inventive system, KRAS gene sequences, encompassing codons 12 and 13, were amplified using 5'-biotin forward and 5'-tagged reverse primers. In the preferred embodiment, a single-stranded PCR fragment was obtained by thermal denaturation of biotinylated PCR products bound to streptavidin-coated magnetic beads. In the preferred embodiment, the single-stranded DNA was hybridized in solution with specific dual-domain reporter probes and captured on a microarray surface through hybridization of the reporter barcode domain with its complementary immobilized probe sequence. In the preferred embodiment, the unexpectedly good results indicate that all the seven codon 12 and 13 mutations studied could be unambiguously detected in less than 90 minutes in tissue clinical samples. Moreover, this system could reveal mutant alleles representing less than 0.1% of the starting material. By decoupling the mutation detection from the array hybridization, this technology becomes universal. Thus, genotyping of the KRAS mutations is only one example of all the possible applications in molecular diagnostic. The dual-domain reporter can be based on a core, such as a dendrimer molecule, which is surface functionalized. This can enhance sensitivity.

TABLE 1

Sequence of spotted probes and reporters for KRAS mutations
KRAS Mutations

| (Amino acid change) | Spotted capture probes[1] | Reporter sequences | Hybr. Temp. (C.°) |
|---|---|---|---|
| Exon 2 Codon12-13 | | | |
| Wild-type | 5'-actccagtgccaagtacgat-3' (SEQ ID NO. 11) | 5'-*CTGGTGGCGTA-<br>†atcgtacttggcactggagt-3' (SEQ ID NO. 19) | |
| c.35G > C (p.G12A) | 5'-cgatccgattacaggccgat-3' (SEQ ID NO. 12) | 5'-*TGGAGCTG<u>C</u>TG-<br>†atcggcctgtaatcggatcg-3' (SEQ ID NO. 20) | 30 |

TABLE 1-continued

Sequence of spotted probes and reporters for KRAS mutations
KRAS Mutations

| | | | |
|---|---|---|---|
| c.34G > T (p.G12C) | 5'-taatcttaattctggtcgcgg-3' (SEQ ID NO. 13) | 5'-CTTGTGGCGTAG-†ccgcgaccagaattagatta-3' (SEQ ID NO. 21) | 41 |
| c.35G > A (p.G12D) | 5'-ggctcacgtcttatttgggc-3' (SEQ ID NO. 14) | 5'-*GCTGATGGCGT-†gcccaaataagacgtgagcc-3' (SEQ ID NO. 22) | 41 |
| c.34 > C (P.G12R) | 5'-tcttctagttgtcgagcagg-3' (SEQ ID NO. 15) | 5'-*CTCGTGGCGTA-†cctgctcgacaactagaaga-3' (SEQ ID NO. 23) | 30 |
| c.34G > A (p.G12S) | 5'-atttgaccaaactgcggtgcg-3' (SEQ ID NO. 16) | 5'-*GCTAGTGGCGTA-†cgcaccgcagtttggtcaat-3' (SEQ ID NO. 24) | 36 |
| c.35G > T (p.G12V) | 5'-tgccctattgttgcgtcgga-3' (SEQ ID NO. 17) | 5'-*AGCTGTTGGCG-†tccgacgcaacaatagggca-3' (SEQ ID NO. 25) | 29 |
| c.38G < A (p.G13D) | 5'-ctcatcggaagggctcgtaa-3' (SEQ ID NO. 18) | 5'-*CTGGTGACGTAGG-†ttacgagcccttccgatgag-3' (SEQ ID NO. 26) | 36 |
| Universal-Cy3[2] | | 5'-ctcaatgttcggactcag-3' (SEQ ID NO. 27) | |
| Stabilizer sequence | | 5'-gcaagagtgccttgacgatacagctattcag-3' (SEQ ID NO. 28) | |

| (Amino acid change) | Spotted capture probes[1] | Reporter sequences | |
|---|---|---|---|
| Exon 3 Codon61 | | | |
| Wild-type | 5'-gcctcgggcaaacgactaaa-3' (SEQ ID NO. 29) | 5'-*AGGTCAAGAGGAG-†tttagtcgtttgcccgaggc-3' (SEQ ID NO. 35) | |
| c.183A > C (Q61HC) | 5'-caccgacgctaatagttaag-3' (SEQ ID NO. 30) | 5'-*GTCACGAGGAGTA-†cttaactattagcgtcggtg-3' (SEQ ID NO. 36) | |
| c.183A > T (Q61HT) | 5'-catacgcggtaaggatatag-3' (SEQ ID NO. 31) | 5-*AGGTCATGAGGAG-†ctatatccttaccgcgtatg-3' (SEQ ID NO. 37) | |
| c.182A > T (Q61L) | 5'-aatgctcgggaaggctactc-3' (SEQ ID NO. 32) | 5-*GGTCTAGAGGAGTA-†gagtagccttcccgagcatt-3' (SEQ ID NO. 38) | |
| c.182A > G (Q61R) | 5'-tcttgacggaaaggtagaca-3' (SEQ ID NO. 33) | 5-*AGGTCGAGAGGA-†tgtctacctttccgtcaaga-3' (SEQ ID NO. 39) | |
| c.181C > A (Q61K) | 5'-atcccgtgagtcgatggttt-3' (SEQ ID NO. 34) | 5-*AGGTAAAGAGGAGTA-†aaaccatcgactcacgggat-3' (SEQ ID NO. 40) | |
| Stabilizer sequence1 | | 5'-gtgtttctcccttctcaggattcctacaggaag-3' (SEQ ID NO. 41) | |
| Stabilizer sequence2 | | 5'-gagaaacctgtctcttggatattctcgacacag-3' (SEQ ID NO. 42) | |
| Exon 4 Codon146 | | | |
| Wild-type | 5'-cgcaccgcagtttggtcaat-3' (SEQ ID NO. 43) | 5'-*CATCAGCAAAGACA-†attgaccaaactgcggtgcg-3' (SEQ ID NO. 45) | |
| c.436G > A (A146T) | 5'-cacgcggcagtcgagttaat-3' (SEQ ID NO. 44) | 5'-*ACATCAACAAAGACA-†attaactcgactgccgcgtg-3' (SEQ ID NO. 46) | |
| Stabilizer sequence | | 5'-gacaggacttagcaagaagttatggaattcattta-3' (SEQ ID NO. 47) | |

[1]The spotted capture probes are amino modified in 5'-end;
*sequences which hybridize to single strand PCR (the variant base for each mutation is in bold and underlined);
†the tails of the reporter oligonucleotides which hybridize to spotted capture probes.
2The universal-Cy3 is labeled with Cyanine 3 in 3'-end.
Nucleotide numbering reflects cDNA numbering with +1 corresponding to the A of the ATG translation initiation codon in the reference GenBank sequence (NM_033360.2). The initiation codon is 1.

TABLE 2

Sequence of spotted probes and reporters for BRAF mutation
BRAF Mutation
Exon 15 Codon 600

| (Amino acid change) | Spotted capture probes[1] | Reporter sequences |
|---|---|---|
| Wild-type | 5'-agcccggtctcatcgttgtt-3' (SEQ ID NO. 48) | 5'-*GCTACAGTGAAATCT-†aacaacgatgagaccgggct-3' (SEQ ID NO. 50) |
| c.1799T > A (V600) | 5'-agggatatgatacgtgcctt-3' (SEQ ID NO. 49) | 5'-*GCTACAGAGAAATCT-†aaggcacgtatcatatccct-3' (SEQ ID NO. 51) |
| Stabilizer sequence1 | 5'-cgatggagtgggtcccatcagtttgaa-3' (SEQ ID NO. 52) | |
| Stabilizer sequence2 | 5'-gaagacctcacagtaaaaataggtgattaggtcta-3' (SEQ ID NO. 53) | |

[1]The spotted capture probes are amino modified in 5'-end;
*sequences which hybridize to single strand PCR (the variant base for each mutation is in bold and underlined);
†-the tails of the reporter oligonucleotides which hybridize to spotted capture probes.
2The universal-Cy3 is labeled with Cyanine 3 in 3'-end.
Nucleotide numbering reflects cDNA numbering with +1 corresponding to the A of the ATG translation initiation codon in the reference GenBank sequence (NM_033360.2). The initiation codon is 1.

TABLE 3

Sequence of spotted probes and reporters for PIK3CA mutations
PIK3CA Mutations

| (Amino acid change) | Spotted capture probes[1] | Reporter sequences |
|---|---|---|
| Exon 9 Codon542 | | |
| Wild-type | 5'-agggctctattcagcgtatt-3' (SEQ ID NO. 54) | 5'-*TCTCTCTGAAATCAC-†aatacgctgaatagagccct-3' (SEQ ID NO. 56) |
| c.1624G > A (E542K) | 5'-gcgcctgtattaggatatgt-3' (SEQ ID NO. 55) | 5'-*CTCTCTCTAAAATCACT-†acatatcctaatacaggcgc-3' (SEQ ID NO. 57) |
| Stabilizer sequence | 5'-atgacaaagaacagctcaaagcaatttctacacgagatc-3' (SEQ ID NO. 58) | |
| Exon 9 Codon545 | | |
| Wild-type | 5'-catcgagtataaggatcgtc-3' (SEQ ID NO. 59) | 5'-*AAATCACTGAGCAG-†gacgatccttatactcgatg-3' (SEQ ID NO. 61) |
| c.1633G > A (E545K) | 5'-gcatgggtataactgtcttc-3' (SEQ ID NO. 60) | 5'-*AAATCACTAAGCAGG-†gaagacagttatacccatgc-3' (SEQ ID NO. 62) |
| Stabilizer sequence | 5'-atgacaaagaacagctcaaagcaatttctacacgagatc-3' (SEQ ID NO. 63) | |
| Exon 20 Codon1047 | | |
| Wild-type | 5'-cgcggagtatagagctttat-3' (SEQ ID NO. 64) | 5'-*ATGCACATCATGG-†ataaagctctatactccgcg-3' (SEQ ID NO. 66) |
| c.3140A > G (H1047R) | 5'-cgagtgcttagatgctagtt-3' (SEQ ID NO. 65) | 5'-*GCACCGTCATGG-†aactagcatctaagcactgc-3' (SEQ ID NO. 67) |

TABLE 3-continued

Sequence of spotted probes and reporters for PIK3CA mutations
PIK3CA Mutations

| (Amino acid change) | Spotted capture probes[1] | Reporter sequences |
|---|---|---|
| Stabilizer sequence1 | 5'-gatgacattgcatacattcgaaagaccctagc-3' (SEQ ID NO. 68) | |
| Stabilizer sequence2 | 5'-ggctggacaacaaaaatggattggatcttc-3' (SEQ ID NO. 69) | |

[1]The spotted capture probes are amino modified in 5'-end;
*sequences which hybridize to single strand PCR (the variant base for each mutation is in bold and underlined);
†the tails of the reporter oligonucleotides which hybridize to spotted capture probes.
2The universal-Cy3 is labeled with Cyanine 3 in 3'-end.
Nucleotide numbering reflects cDNA numbering with +1 corresponding to the A of the ATG translation initiation codon in the reference GenBank sequence (NM_033360.2). The initiation codon is 1.

TABLE 4

Sequence of spotted probes and reporters for NRAS mutations
NRAS Mutations
Exon 2 Codon12-13

| (Amino acid change) | Spotted capture probes[1] | Reporter sequences |
|---|---|---|
| Wild-type | 5'-cgagcacttaacattagagc-3' (SEQ ID NO. 70) | 5'-*AGCAGGTGGTG-†gctctaatgttaagtgctcg-3' (SEQ ID NO. 79) |
| c.35G > C (p.G12A) | 5'-tccgaccttcgatctgtggt-3' (SEQ ID NO. 71) | 5'-*AGCAGCTGGTG-†accacagatcgaaggtcgga-3' (SEQ ID NO. 80) |
| c.34G > T (p.G12C) | 5'-atcgtacttggcactggagt-3' (SEQ ID NO. 72) | 5'-*GAGCATGTGGTG-†actccagtgccaagtacgat-3' (SEQ ID NO. 81) |
| c.35G > A (p.G12D) | 5'-cgccgtatatggtcattggt-3' (SEQ ID NO. 73) | 5'-*AGCAGATGGTGTT-†accaatgaccatatacggcg-3' (SEQ ID NO. 82) |
| c.34G > A (p.G12S) | 5'-gcccaaataagacgtgagcc-3' (SEQ ID NO. 74) | 5'-*GAGCAAGTG GTG-†ggctcacgtcttatttgggc-3' (SEQ ID NO. 83) |
| c.35G > T (p.G12V) | 5'-actcaaacataactctggcg-3' (SEQ ID NO. 75) | 5'-*AGCAGTTGGTGT-†cgccagagttatgtttgagt-3' (SEQ ID NO. 84) |
| c.38G> A (p.G13D) | 5'-acgagcgcataccatcgaag-3' (SEQ ID NO. 76) | 5'-*AGCAGGTGATGTT-†cttcgatggtatgcgctcgt-3' (SEQ ID NO. 85) |
| c.37G > C (p.G13R) | 5'-tccgacgcaacaatagggca-3' (SEQ ID NO. 77) | 5'-GCAGGTCGTGT-†tgccctattgagcgtcgga-3' (SEQ ID NO. 86) |
| c.38G > T (p.G13V) | 5'-cctgctcgacaactagaaga-3' (SEQ ID NO. 78) | 5'-*AGCAGGTGTTGT-†tcttctagttgtcgagcagg-3' (SEQ ID NO. 87) |
| Stabilizer sequence | | 5'-ctgacaatccagctaatccagaaccactttgta-3' (SEQ ID NO. 88) |

[1]The spotted capture probes are amino modified in 5'-end;
*sequences which hybridize to single strand PCR (the variant base for each mutation is in bold and underlined);
†the tails of the reporter oligonucleotides which hybridize to spotted capture probes.
2The universal-Cy3 is labeled with Cyanine 3 in 3'-end.
Nucleotide numbering reflects cDNA numbering with +1 corresponding to the A of the ATG translation initiation codon in the reference GenBank sequence (NM_033360.2). The initiation codon is 1.

What is claimed is:

1. An assay for detecting single-nucleotide polymorphisms (SNPs) in gene fragments, the assay comprising:
   amplifying gene fragments to form an initial amplification product;
   isolating single strand deoxyribose nucleic acid (ssDNA) from the initial amplification product;
   forming a solution comprising the ssDNA and different reporter molecules, each reporter molecule comprising a first domain configured to hybridize with a wild-type or mutated nucleotide sequence that may potentially be included in the ssDNA, the mutated nucleotide sequences each comprising a SNP, and a corresponding second domain configured to hybridize with a complementary capture probe;
   hybridizing, in the solution, the ssDNA with the reporter molecules that have first domains that are complementary to the ssDNA;
   applying the solution to the surface of a microarray comprising an array of capture probes fixed to a microarray slide, each capture probe being configured to hybridize with a complementary second domain of a corresponding reporter molecule;
   capturing the hybridized ssDNA on the microarray by hybridizing the second domains of the reporter molecules with complementary capture probes of the microarray; and
   detecting the hybridized ssDNA captured on the microarray.

2. The assay of claim 1, wherein the gene fragments to be amplified are primed in the amplification to enable the detecting of the hybridized ssDNA.

3. The assay of claim 1, wherein the gene fragments to be amplified are primed in the amplification to enable the isolating of the ssDNA and the detecting of the hybridized ssDNA.

4. The assay of claim 1, wherein the assay and the gene fragments are for the detection of at least one single mutation in a KRAS, NRAS, BRAF, and/or PIK3CA oncogene.

5. The assay of claim 1, wherein the array of capture probes comprises capture probes having different nucleotide sequences arranged on corresponding areas of the microarray slide.

6. The assay of claim 1, wherein the assay and the gene fragments are for detection of at least one single mutation in an NRAS oncogene.

7. The assay of claim 1, wherein the assay and the gene fragments are for the detection of at least one single mutation in a BRAF oncogene.

8. The assay of claim 1, wherein the assay and the gene fragments are for the detection of at least one single mutation in a PIK3CA oncogene.

9. The assay of claim 1, wherein:
the amplifying gene fragments comprises using binding primers to form the ssDNA; and
the isolating the ssDNA comprises linking the binding primers of the ssDNA to beads and using a magnet to capture the beads and isolate the ssDNA.

10. The assay of claim 1, wherein the amplifying gene fragments comprises linking a fluorescent tag to the ssDNA.

11. The assay of claim 1, wherein amplifying gene fragments comprises linking particles to the ssDNA that enable interferometric detection of the oligonucleotides of interest.

12. The assay of claim 1, wherein the amplifying comprises polymerase chain reaction (PCR) amplification.

13. The assay of claim 1, wherein the isolating ssDNA single comprises thermal denaturation of the initial amplification product.

14. The assay of claim 1, wherein the isolating ssDNA comprises chemical denaturation of the initial amplification product.

15. The assay of claim 1, wherein the hybridizing comprises hybridizing, in the solution, the ssDNA with first reporter molecules that have first domains that have a first nucleotide sequence, by maintaining the solution at a first hybridization temperature corresponding to the first sequence for a first time period, and hybridizing, in the solution, the ssDNA with a second type of the reporter molecules that have first domains that have a second nucleotide sequence, by maintaining the solution at a different second hybridization temperature corresponding to the second nucleotide sequence for a second time period.

16. The assay of claim 1, further comprising stabilizing the ssDNA prior to the hybridizing, in the solution, the ssDNA.

17. The assay of claim 1, wherein the microarray slide comprises a terpolymer coating that binds to the capture probes.

18. An assay for detecting single-nucleotide polymorphisms (SNPs) in gene fragments, the assay comprising:
amplifying gene fragments to form an initial amplification product, wherein the amplifying comprises using reverse primers configured to hybridize with fluorescent oligonucleotides;
isolating single strand deoxyribose nucleic acid (ssDNA) from the initial amplification product, the ssDNA including the reverse primers;
forming a solution comprising the ssDNA and reporting molecules, each reporting molecule comprising a first domain configured to hybridize with a wild-type or mutated sequence that may potentially be included in the ssDNA, the mutated sequences each comprising a SNP, and a second oligonucleotide domain configured to hybridize with a complementary capture probe;
hybridizing, in the solution, the ssDNA with the reporter molecules that have first domains that arm complementary to the ssDNA;
applying the solution to the surface of a microarray comprising an array capture probes fixed to a microarray slide, each capture probe being configured to hybridize with a complementary second domain of a corresponding reporter molecule;
capturing the hybridized ssDNA on the microarray by hybridizing the second oligonucleotide domains of the reporter molecules with complementary capture probes of the microarray; and
detecting the hybridized ssDNA captured on the array by detecting fluorescent oligonucleotides hybridized with the primers.

19. An assay for detecting single-nucleotide polymorphisms (SNPs) in gene fragments, the assay comprising:
amplifying gene fragments to form an initial amplification product;
isolating single strand deoxyribose nucleic acid (ssDNA) from the initial amplification product;
forming a solution comprising the ssDNA and different reporting molecules, each reporting molecule comprising a first domain configured to hybridize with a wild-type or mutated sequence that may potentially be included in the ssDNA, the mutated sequences each comprising a SNP, and a corresponding second oligonucleotide domain configured to hybridize with a complementary capture probe;
hybridizing, in the solution, the ssDNA with first reporter molecules that have first domains that have a first nucleotide sequence, by maintaining the solution at a first hybridization temperature corresponding to the first sequence for a first time period, and hybridizing, in the solution, the ssDNA with a second type of the reporter molecules that have first domains that have a second nucleotide sequence, by maintaining the solution at a different second hybridization temperature corresponding to the second nucleotide sequence for a second time period;
applying the solution to the surface of a microarray comprising an array capture probes fixed to a microarray slide, each capture probe being configured to hybridize with a complementary second domain of a corresponding reporter molecule;
capturing the hybridized ssDNA on the microarray by hybridizing the second oligonucleotide domains of the reporter molecules with complementary capture probes of the microarray; and
detecting the hybridized ssDNA captured on the array.

20. The assay of claim 19, wherein the hybridizing further comprises hybridizing, in the solution, the ssDNA with a third type of the reporter molecules that have first domains that are complementary to the ssDNA that has a third sequence, by maintaining the solution at a third hybridization temperature for a third time period.

21. The assay of claim 19, wherein the isolating ssDNA comprises:
coupling the ssDNA to beads; and
using a magnet to manipulate the beads and isolate the ssDNA.

* * * * *

SEQUENCE LISTING

<160> NUMBER OF SEQ ID NOS: 88

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
gcctgctgaa aatgactgaa                                               20

<210> SEQ ID NO 2
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
ctgagtccga acattgagag aatggtcctg caccagtaa                          39

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 3
actccagtgc caagtacgat                                               20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 4
ggctcacgtc ttatttgggc                                               20

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
atcgtacttg gcactggagt                                               20

<210> SEQ ID NO 6
<211> LENGTH: 11
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 6
ctggtggcgt a                                                           11

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gcccaaataa gacgtgagcc                                                  20

<210> SEQ ID NO 8
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gctgatggcg t                                                           11

<210> SEQ ID NO 9
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
ctcaatgttc ggactcag                                                    18

<210> SEQ ID NO 10
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
tacgccacca g                                                           11

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 11
actccagtgc caagtacgat                                                  20

<210> SEQ ID NO 12
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 12
cgatccgatt acaggccgat                                              20

<210> SEQ ID NO 13
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 13
taatcttaat tctggtcgcg g                                            21

<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 14
ggctcacgtc ttatttgggc                                              20

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 15
tcttctagtt gtcgagcagg                                              20

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 16
atttgaccaa actgcggtgc g                                            21

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 17
```

```
tgccctattg ttgcgtcgga                                              20
```

<210> SEQ ID NO 18
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 18

```
ctcatcggaa gggctcgtaa                                              20
```

<210> SEQ ID NO 19
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19

```
ctggtggcgt aatcgtactt ggcactggag t                                 31
```

<210> SEQ ID NO 20
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20

```
tggagctgct gatcggcctg taatcggatc g                                 31
```

<210> SEQ ID NO 21
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21

```
cttgtggcgt agccgcgacc agaattagat ta                                32
```

<210> SEQ ID NO 22
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22

```
gctgatggcg tgcccaaata agacgtgagc c                                 31
```

<210> SEQ ID NO 23
<211> LENGTH: 31
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 23
ctcgtggcgt acctgctcga caactagaag a                                31

<210> SEQ ID NO 24
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
gctagtggcg tacgcaccgc agtttggtca at                               32

<210> SEQ ID NO 25
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
agctgttggc gtccgacgca acaatagggc a                                31

<210> SEQ ID NO 26
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
ctggtgacgt aggttacgag cccttccgat gag                              33

<210> SEQ ID NO 27
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
ctcaatgttc ggactcag                                               18

<210> SEQ ID NO 28
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
gcaagagtgc cttgacgata cagctattca g                                31
```

```
<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 29
gcctcgggca aacgactaaa                                                 20

<210> SEQ ID NO 30
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 30
caccgacgct aatagttaag                                                 20

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 31
catacgcggt aaggatatag                                                 20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 32
aatgctcggg aaggctactc                                                 20

<210> SEQ ID NO 33
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 33
tcttgacgga aaggtagaca                                                 20

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
```

```
<400> SEQUENCE: 34
atcccgtgag tcgatggttt                                              20

<210> SEQ ID NO 35
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
aggtcaagag gagtttagtc gtttgcccga ggc                               33

<210> SEQ ID NO 36
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
gtcacgagga gtacttaact attagcgtcg gtg                               33

<210> SEQ ID NO 37
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
aggtcatgag gagctatatc cttaccgcgt atg                               33

<210> SEQ ID NO 38
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
ggtctagagg agtagagtag ccttcccgag catt                              34

<210> SEQ ID NO 39
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
aggtcgagag gatgtctacc tttccgtcaa ga                                32

<210> SEQ ID NO 40
<211> LENGTH: 35
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic oligonucleotide"

<400> SEQUENCE: 40
aggtaaagag gagtaaaacc atcgactcac gggat         35

<210> SEQ ID NO 41
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
gtgtttctcc cttctcagga ttcctacagg aag            33

<210> SEQ ID NO 42
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
gagaaacctg tctcttggat attctcgaca cag            33

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 43
cgcaccgcag tttggtcaat                           20

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 44
cacgcggcag tcgagttaat                           20

<210> SEQ ID NO 45
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
catcagcaaa gacaattgac caaactgcgg tgcg           34

<210> SEQ ID NO 46
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
acatcaacaa agacaattaa ctcgactgcc gcgtg                                35

<210> SEQ ID NO 47
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
gctcaggact tagcaagaag ttatggaatt cctttta                              37

<210> SEQ ID NO 48
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 48
agcccggtct catcgttgtt                                                 20

<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 49
agggatatga tacgtgcctt                                                 20

<210> SEQ ID NO 50
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
gctacagtga aatctaacaa cgatgagacc gggct                                35

<210> SEQ ID NO 51
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
gctacagaga aatctaaggc acgtatcata tccct                                35

<210> SEQ ID NO 52
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
cgatggagtg ggtcccatca gtttgaa                                         27

<210> SEQ ID NO 53
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
gaagacctca cagtaaaaat aggtgatttt ggtcta                               36

<210> SEQ ID NO 54
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 54
agggctctat tcagcgtatt                                                 20

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 55
gcgcctgtat taggatatgt                                                 20

<210> SEQ ID NO 56
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
tctctctgaa atcacaatac gctgaataga gccct                                35

<210> SEQ ID NO 57
<211> LENGTH: 37
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
ctctctctaa aatcactaca tatcctaata caggcgc                               37

<210> SEQ ID NO 58
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
atgacaaaga acagctcaaa gcaatttcta cacgagatc                             39

<210> SEQ ID NO 59
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 59
catcgagtat aaggatcgtc                                                  20

<210> SEQ ID NO 60
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 60
gcatgggtat aactgtcttc                                                  20

<210> SEQ ID NO 61
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
aaatcactga gcaggacgat ccttatactc gatg                                  34

<210> SEQ ID NO 62
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
aaatcactaa gcagggaaga cagttatacc catgc                                 35
```

<210> SEQ ID NO 63
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
atgacaaaga acagctcaaa gcaatttcta cacgagatc                39

<210> SEQ ID NO 64
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 64
cgcggagtat agagctttat                                     20

<210> SEQ ID NO 65
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 65
cgagtgctta gatgctagtt                                     20

<210> SEQ ID NO 66
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
atgcacatca tggataaagc tctatactcc gcg                      33

<210> SEQ ID NO 67
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
gcacgtcatg gaactagcat ctaagcactg c                        31

<210> SEQ ID NO 68
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 68
gatgacattg catacattcg aaagaccctc gc                                32

<210> SEQ ID NO 69
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
ggctggacaa caaaaatgga ttggatcttc                                  30

<210> SEQ ID NO 70
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 70
cgagcactta acattagagc                                             20

<210> SEQ ID NO 71
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 71
tccgaccttc gatctgtggt                                             20

<210> SEQ ID NO 72
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 72
atcgtacttg gcactggagt                                             20

<210> SEQ ID NO 73
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 73
cgccgtatat ggtcattggt                                             20

<210> SEQ ID NO 74
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 74
gcccaaataa gacgtgagcc                                                  20

<210> SEQ ID NO 75
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 75
actcaaacat aactctggcg                                                  20

<210> SEQ ID NO 76
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 76
acgagcgcat accatcgaag                                                  20

<210> SEQ ID NO 77
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 77
tccgacgcaa caatagggca                                                  20

<210> SEQ ID NO 78
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 78
cctgctcgac aactagaaga                                                  20

<210> SEQ ID NO 79
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
```
agcaggtggt ggctctaatg ttaagtgctc g        31

<210> SEQ ID NO 80
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
agcagctggt gaccacagat cgaaggtcgg a        31

<210> SEQ ID NO 81
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
gagcatgtgg tgactccagt gccaagtacg at       32

<210> SEQ ID NO 82
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
agcagatggt gttaccaatg accatatacg gcg      33

<210> SEQ ID NO 83
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
gagcaagtgg tgggctcacg tcttatttgg gc       32

<210> SEQ ID NO 84
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
agcagttggt gtcgccagag ttatgtttga gt       32

<210> SEQ ID NO 85
<211> LENGTH: 33
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 85
agcaggtgat gttcttcgat ggtatgcgct cgt                              33

<210> SEQ ID NO 86
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
gcaggtcgtg ttgccctatt gttgcgtcgg a                                31

<210> SEQ ID NO 87
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
agcaggtgtt gttcttctag ttgtcgagca gg                               32

<210> SEQ ID NO 88
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
ctgacaatcc agctaatcca gaaccactttt gta                             33
```